United States Patent [19]
Levine et al.

[11] Patent Number: 6,058,328
[45] Date of Patent: May 2, 2000

[54] IMPLANTABLE STIMULATION DEVICE HAVING MEANS FOR OPERATING IN A PREEMPTIVE PACING MODE TO PREVENT TACHYARRHYTHMIAS AND METHOD THEREOF

[75] Inventors: Paul A. Levine, Newhall; Jason A. Sholder, Beverly Hills; Gene A. Bornzin, Simi Valley; Joseph J. Florio, Sunland; Kenneth Valikai, Palos Verdes Pen.; Lisa P. Weinberg, Moorpark, all of Calif.

[73] Assignee: Pacesetter, Inc., Sylmar, Calif.

[21] Appl. No.: 08/788,152

[22] Filed: Jan. 24, 1997

Related U.S. Application Data

[60] Provisional application No. 60/023,463, Aug. 6, 1996, abandoned.

[51] Int. Cl.⁷ .................................................. A61N 1/362
[52] U.S. Cl. ............................................................ 607/14
[58] Field of Search ................................ 607/4, 5, 14, 15

[56] References Cited

U.S. PATENT DOCUMENTS

| | | | |
|---|---|---|---|
| 4,548,209 | 10/1985 | Wielders | 128/419 |
| 4,572,192 | 2/1986 | Jackman et al. | 607/14 |
| 4,693,253 | 9/1987 | Adams | 128/419 |
| 4,712,555 | 12/1987 | Thornander | 128/419 |
| 4,788,980 | 12/1988 | Mann | 128/419 |
| 4,940,052 | 7/1990 | Mann | 128/419 |
| 4,944,298 | 7/1990 | Sholder | 128/419 |
| 4,958,632 | 9/1990 | Duggan | 128/419 |
| 5,042,497 | 8/1991 | Shapland | 607/14 |
| 5,103,822 | 4/1992 | Duncan | 128/419 |
| 5,188,105 | 2/1993 | Keimel | 128/419 |
| 5,201,321 | 4/1993 | Fulton | 128/702 |
| 5,330,507 | 7/1994 | Schwartz | 607/14 |
| 5,340,361 | 8/1994 | Sholder | 607/24 |
| 5,342,401 | 8/1994 | Spano | 607/5 |
| 5,425,749 | 6/1995 | Adams | 607/5 |
| 5,447,520 | 9/1995 | Spano | 607/5 |
| 5,456,690 | 10/1995 | Duong-Van | 607/5 |
| 5,466,245 | 11/1995 | Spinelli | 607/17 |
| 5,476,483 | 12/1995 | Bornzin | 607/17 |
| 5,601,609 | 2/1997 | Duncan | 607/14 |

OTHER PUBLICATIONS

Bornzin, et al. "Adjusting Heart Rate During Sleep Using Activity Variance"; *Pace*; 17; pp. 1933–1938; (Nov. 1994).

Murgatroyd, et al. "A New Pacing Algorithm for Overdrive Suppression of Atrial Fibrillation"; *Pace*; 17; pp. 1966–1973; (Nov. 1994).

Cotton, et al. "Chaos, Other Nonlinear Dynamics Research May Have Answers, Applications for Clinical Medicine"; *JAMA*; 266, No. 1; pp. 12–18; (Jul. 1991).

Smith, et al. "Electrical Alternans and Cardiac Electrical Instability"; *Circulation*; 77, No. 1; pp. 110–121; (Jan. 1988).

*Primary Examiner*—William E. Kamm

[57] ABSTRACT

Preemptive tachyarrhythmia pacing is provided in an implantable cardiac-stimulation device, such as an implantable pacemaker or defibrillator, by modifying the operation of the implantable device in a way that minimizes the likelihood of occurrence of a tachyarrhythmia. The behavior modification is achieved through the use of an appropriate preemptive tachyarrhythmia pacing control routine stored within the memory of the device. Depending upon the needs of the patient, preemptive tachyarrhythmia pacing is invoked continuously or on demand. If invoked on demand, Preemptive tachyarrhythmia pacing is triggered only upon the sensing of one or more conditions suggest that the onset of a tachyarrhythmia is imminent. When thus invoked, preemptive tachyarrhythmia pacing remains invoked only for as long as the onset-of-a-tachyarrhythmia-is-imminent conditions persist. Various preemptive tachyarrhythmia pacing control routines are contemplated, including those based on overdrive pacing, pacing with randomicity, and mode switching. Overdrive pacing, when used, is based on an automatically-determined diurnal rate, an automatic stepped increase over the average atrial rate, or a rate set by a cycle-to-cycle negative hysteresis. Conditions which suggest the imminency of the onset of a tachyarrhythmia include, but are not limited to, a sudden change in the patient's cardiac cycle from a previously-determined normal cardiac cycle.

62 Claims, 13 Drawing Sheets

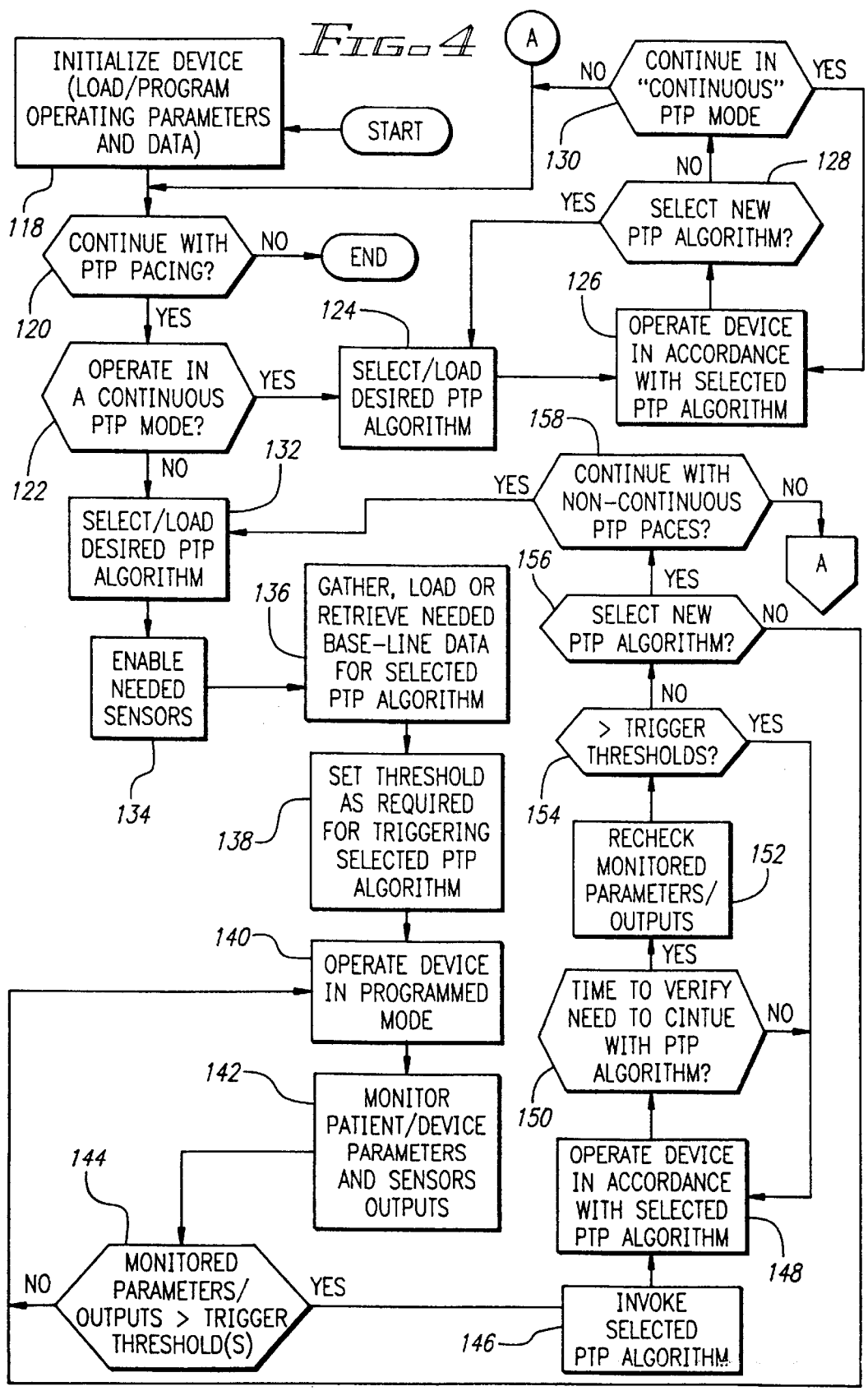

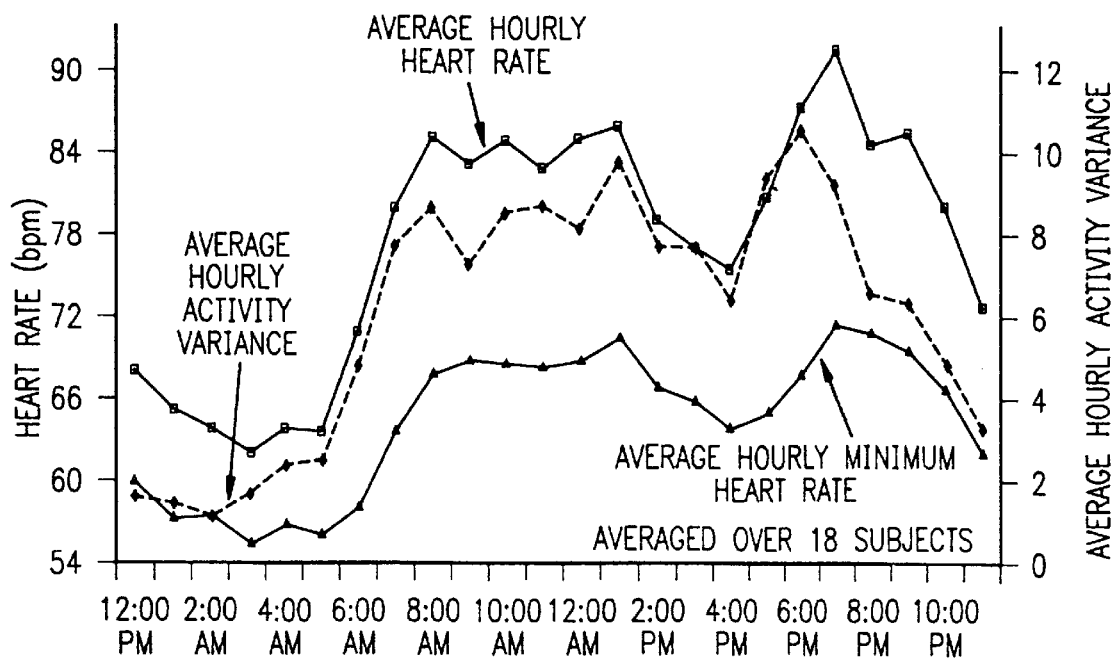

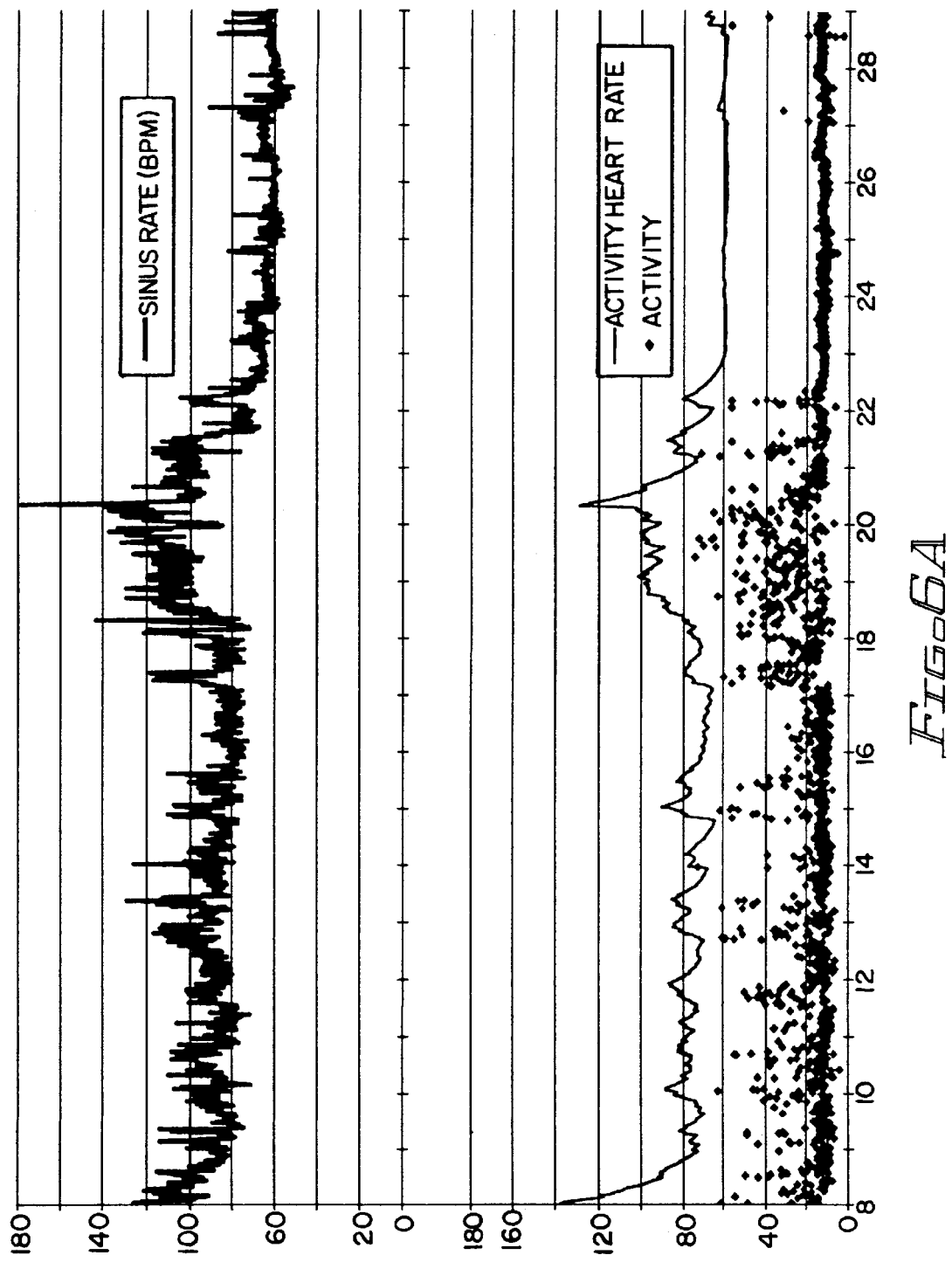

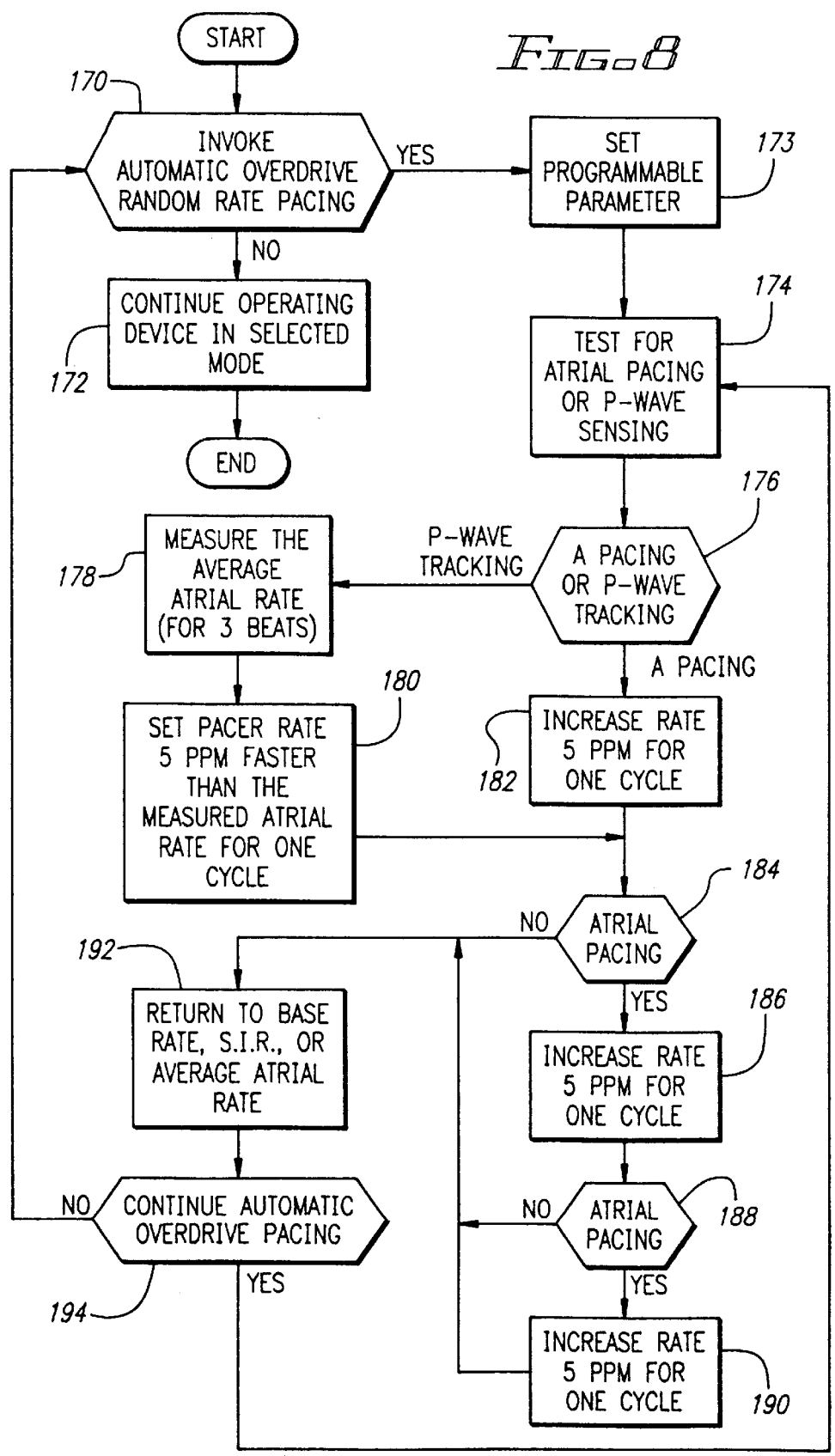

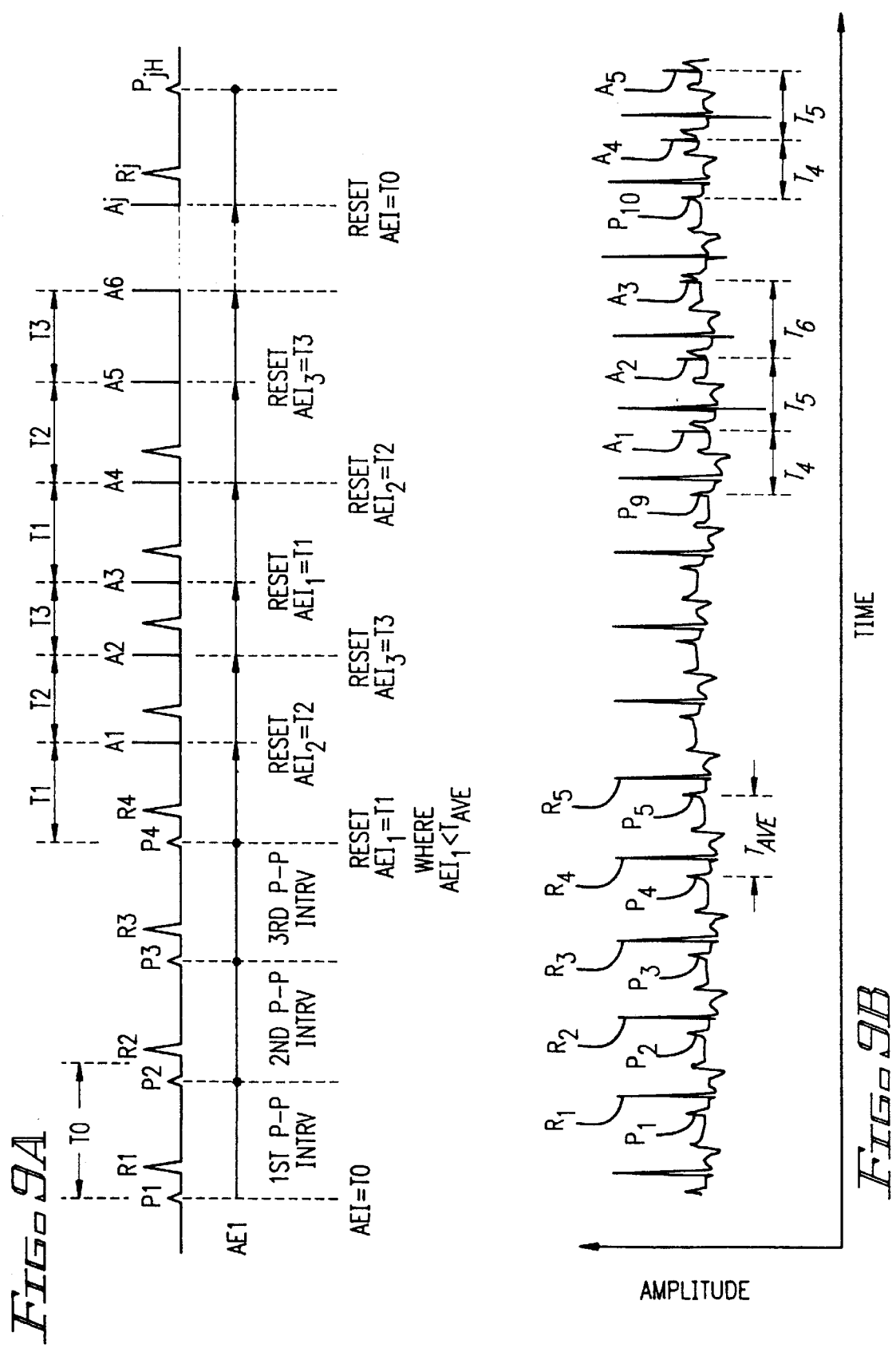

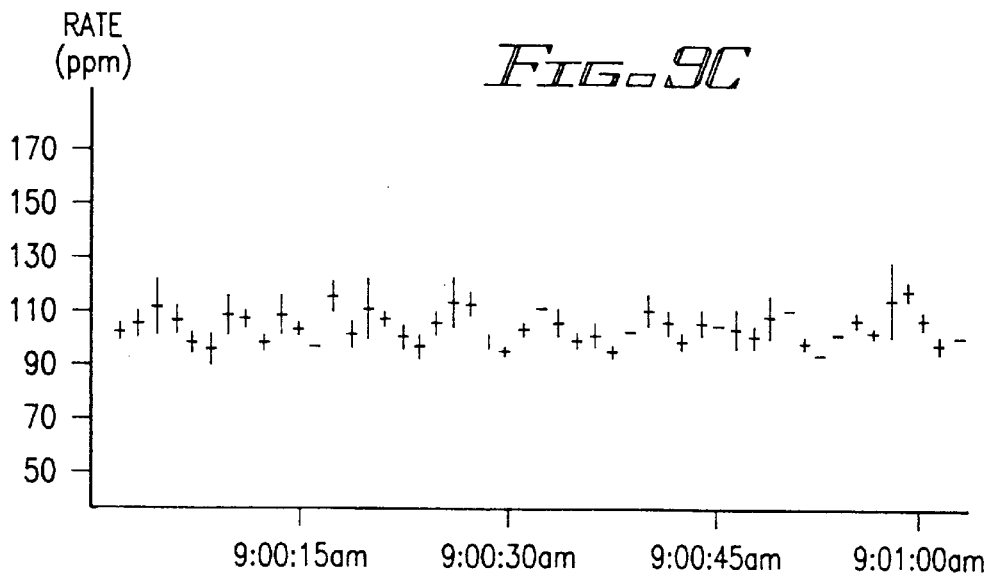
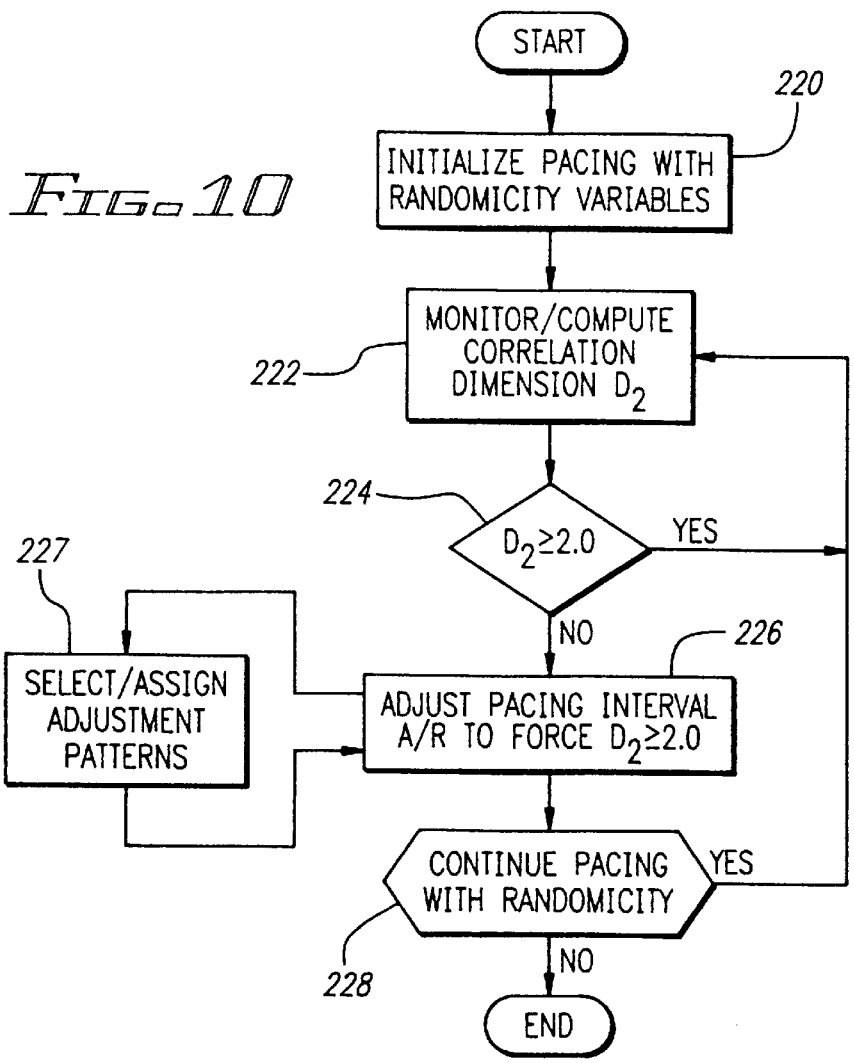

IMPLANTABLE STIMULATION DEVICE HAVING MEANS FOR OPERATING IN A PREEMPTIVE PACING MODE TO PREVENT TACHYARRHYTHMIAS AND METHOD THEREOF

This application claims the benefit of U.S. Provisional Application No. 60/023,463 Aug. 6, 1996, now abandoned.

FIELD OF THE INVENTION

The present invention relates to implantable medical devices and methods, e.g., implantable pacemakers or defibrillators, and more particularly to preemptive tachyarrhythmia pacing algorithms or techniques for use within such implantable medical devices. The invention further relates to methods for best determining when such preemptive tachyarrhythmia pacing algorithms should be triggered or evoked in order to prevent the occurrence of a tachyarrhythmia.

BACKGROUND OF THE INVENTION

A well known adage states "an ounce of prevention is worth a pound of cure." Despite the wisdom offered by this adage, most implantable stimulator devices available today, e.g., pacemakers or defibrillators, are "reactive" devices. Only pharmacologic therapy (with its accompanying undesirable side effects) has made any serious attempt at preventative therapy. Implantable devices, on the other hand, are predominantly reactive. That is, such devices are designed to sense certain conditions perceived as undesirable or dangerous to a particular patient, such as a tachyarrhythmia, bradycardia, or fibrillation, and then respond to such sensed undesirable condition by automatically issuing one or more prescribed stimulation or defibrillation pulses, at prescribed rates and energy levels, in an effort to quickly terminate or stop the sensed undesirable condition. U.S. Pat. Nos. 4,548,209; 4,693,253; 4,788,980; 5,103,822; 5,188,105; for example, are illustrative of the numerous patents that exist which disclose reactive-type pacemakers that (1) sense a tachyarrhythmia and (2) react to the sensed tachyarrhythmia in an effort to quickly terminate it.

For many patients, i.e., those particularly prone or susceptible to experiencing the undesirable or potentially dangerous conditions mentioned above—tachyarrhythmia, bradycardia, or fibrillation—, it would be much more desirable to prevent the undesirable condition rather than to simply treat it (by trying to stop it) once it has occurred. Unfortunately, the only types of preventative management that have been regularly practiced in the art are fraught with difficulties and/or undesirable side effects. Such prior preventative management techniques include: pharmacologic therapy, with a high incidence of side effects (some of which are life threatening); or physically interrupting a critical conduction pathway, which first requires a complex electrophysiologic study followed by either catheter ablation or an open heart surgical operation. On occasion, pacing at a relatively rapid rate (overdrive suppression) has been effective as a preventative tool, but this unfortunately obligates the patient to being paced rapidly at times when such rapid pacing may not be required. There is thus a need in the art to identify particular pacing or stimulation strategies that, when used, prevent the onset of, or at least minimize the likelihood of occurrence of, a tachyarrhythmia or other perceived undesirable condition, and which apply such stimulation strategies only when needed and only for so long as needed.

One prior art implantable defibrillator device, disclosed in U.S. Pat. No. 5,425,749, provides a single preemptive charge to a patient's heart within a few seconds after having either detected or predicted the onset of an arrhythmia, instead of waiting up to 25 seconds to confirm an arrhythmia and then deliver a large shock. If the single preemptive charge is ineffective, then conventional detection/confirmation of the arrhythmia continues along with the more time consuming charging of a large output capacitor, and eventual delivery of the large shock. If the single preemptive charge is effective, however, then the large capacitor is not charged. In this way, the preemptive shock is applied sooner, e.g., within 2–3 seconds of when the arrhythmia is first detected or predicted.

The '749 patent teaches that the detection of an arrhythmia may be made by detecting a burst of "n" high rate heartbeats of approximately 200 beats per minute, or by predicting or anticipating the occurrence of fibrillation as described in Droll et al., "Slope Filtered Pointwise Correlation Dimension Algorithm and Evaluation with Prefibrillation Heart Rate Data," *Journal of Electrocardiology*, Vol. 24, Supplement, pp. 97–101. Other techniques mentioned in the '749 patent for detecting or predicting the onset of fibrillation include techniques based on waveform morphology, rate acceleration, or rate stability, although no express teachings are provided for how waveform morphology, rate acceleration, or rate stability could be used for this purpose.

Despite the teaching of the '749 patent that a single preemptive shock could be delivered by an implantable defibrillator device if an arrhythmia is detected or predicted, there remains a critical need in the art to improve upon this technique, and in particular to provide a much lower power and less traumatic pacing regime aimed at preventing an arrhythmia from occurring, including improved techniques for recognizing when and if an arrhythmia is soon likely to occur.

Coupled with the above need (of identifying appropriate preemptive tachyarrhythmia pacing or stimulation strategies) is the need to know when such pacing or stimulation strategies can or should be used to best benefit a given patient. In other words, there is a need to ascertain, for any given patient, whether such preemptive tachyarrhythmia pacing strategies should be employed continuously, or whether such can or should be used selectively, e.g., only when one or more specified parameters, monitored with one or more appropriate sensors, suggest that the onset of a tachyarrhythmia is imminent.

Additional background material relating to the causes of pathologic tachyarrhythmias, and the teachings of the prior art relative to treating such tachyarrhythmias is found in Appendix A, below.

SUMMARY OF THE INVENTION

The present invention addresses the above and other needs by providing preemptive tachyarrhythmia pacing in an implantable cardiac-stimulating device, such as an implantable pacemaker or defibrillator. Preemptive tachyarrhythmia pacing is achieved, in accordance with the invention, by modifying the behavior or operation of the implantable device in a way that prevents (or at least minimizes the likelihood of occurrence of) a tachyarrhythmia, where a "tachyarrhythmia" is broadly defined herein to include any cardiac rhythmic disorder. The modification of the behavior of the cardiac-stimulating device is realized by invoking an appropriate algorithm stored within the memory circuits of the device, and carried out by the control circuits of the device. Depending upon the needs of the patient, the preemptive tachyarrhythmia pacing algorithm may be invoked either continuously, or on demand. If invoked on demand, the Preemptive tachyarrhythmia pacing algorithm is invoked only when triggered by the occurrence of one or more monitored parameters that suggest a tachyarrhythmia could soon occur, and then remains invoked only for as long as is needed, e.g., only while the tachyarrhythmia-could-soon-occur conditions persist.

In accordance with one aspect of the invention, the Preemptive tachyarrhythmia pacing control algorithm is based on overdrive pacing, e.g., atrial overdrive pacing. In overdrive pacing, pacing is provided at a rate which is faster than the patient's underlying rate. Hence, atrial overdrive pacing is achieved by providing an atrial stimulation pulse (referred to herein as an "A-pulse") to the heart at a time in the cardiac cycle that is just prior to the time when a spontaneous atrial depolarization, referred to herein as a "P-wave", would otherwise occur. A sequence of such A-pulses applied to the atria thus cause the atria to depolarize at a time in the cardiac cycle that is slightly before when a spontaneous P-wave would occur, thereby achieving overdrive pacing.

Overdrive pacing, when used, is controlled by one or more physician-selectable overdrive pacing algorithms or routines. Such algorithms provide, e.g., A-pulses at a rate aimed at overpacing the atria based on: (1) an automatically-determined diurnal rate, (2) an automatic stepped increase over average atrial rate, (3) a negative hysteresis scheme, or (4) other suitable techniques.

In a first overdrive pacing algorithm, the overdrive pacing rate, i.e., the rate at which A-pulses are provided to assure that they most always occur in the cardiac cycle just prior to when a natural atrial depolarization (P-wave) would otherwise occur, is based on a predetermined diurnal rate of the patient. Such diurnal rate varies throughout the day, and may be automatically determined, e.g., using the method described in Bornzin et al., "Adjusting Heart Rate During Sleep Using Activity Variance," PACE, Vol. 17, (Pt. II) pp. 1933–1938 (November 1994).

In a second overdrive pacing algorithm, the overdrive pacing rate is set and controlled based on an automatic stepped increase (which may introduce a controlled variability into the resulting heart rate) over the average atrial rate, in the manner described, or similar to that which is described.

In a third overdrive pacing algorithm, the overdrive pacing rate may be set every cardiac cycle using a negative hysteresis scheme.

It is to be emphasized that the primary purpose of providing overdrive pacing in accordance with the invention is to utilize overdrive pacing as a tool (i.e., as part of a preemptive tachyarrhythmia pacing control scheme or algorithm) aimed at preventing the occurrence of tachyarrhythmias. Hence, any overdrive pacing technique now known or yet to be developed that furthers this preemptive purpose may be used advantageously with the invention.

Overdrive pacing is not the only tool contemplated by the present invention for use by a preemptive tachyarrhythmia pacing control scheme or algorithm. For example, the invention also recognizes that an effective tool for preventing tachyarrhythmias is to introduce a certain degree of randomicity into the base rate of the pacemaker or other medical device. Such randomicity may be achieved, for example, by monitoring a correlation dimension associated with the heart rate in accordance with chaos theory, and then varying the stimulation rate on a beat-by-beat basis so that such correlation dimension is always equal to at least a prescribed value, e.g., a value of 2.0 or above. Advantageously, pacing with randomicity may be used either as a preemptive tachyarrhythmia pacing technique by itself, or in combination with overdrive pacing (e.g., the A-pulse provided during atrial overdrive pacing may be provided at a time in the cardiac cycle that is not only prior to when a natural P-wave would otherwise occur, but also at a time that varies with a certain degree of randomicity).

Yet another approach or tool that may be used by the present invention as part of a preemptive tachyarrhythmia pacing algorithm is to switch the pacing mode of the pacemaker (or other implantable medical device) from whatever its current operating mode is to an alternative pacing mode, coupled with an appropriate automatic change in specified pacing/sensing parameters. For example, if the operating mode of a pacemaker is the DDD mode, and if a preemptive tachyarrhythmia pacing triggering event occurs (signaling the need to invoke the preemptive tachyarrhythmia pacing algorithm), then the preemptive tachyarrhythmia pacing algorithm may automatically switch the operating mode of the pacemaker to the DDI mode, coupled with autoprogramming the atrial output to a high value (high amplitude A-pulse) so as to maximize the chance of atrial capture.

When a mode-switching preemptive tachyarrhythmia pacing algorithm is used (e.g., as described in the previous paragraph), each available operating mode of the medical device is programmably mapped to an alternative operating mode which is to be automatically invoked whenever the preemptive tachyarrhythmia pacing algorithm is triggered. If no mode-mapping selections are made, then default selections are automatically imposed so that each operating mode is always mapped to an alternate mode.

A key aspect of the invention relates to determining when the preemptive tachyarrhythmia pacing algorithm, or control scheme, whatever form it may take, is to be used by the medical device. In this regard, another aspect of the invention concerns carefully monitoring the cardiac cycle of a patient in order to "learn" what sequence and/or rate of cardiac events (atrial and/or ventricular) is "normal" for the patient. Thereafter, when specific spontaneous behavior is detected that varies from the patient's learned normal behavior, which spontaneous behavior typically precedes a tachyarrhythmia or other undesirable cardiac rhythmic disorder, the device's operation is automatically varied (i.e, the preemptive tachyarrhythmia pacing algorithm is invoked) for the purpose of preventing a tachyarrhythmia, or other undesirable cardiac rhythmic disorder.

Advantageously, unlike prior art implantable medical devices (which are generally programmed to recognize the onset of a tachyarrhythmia, and then modify the device operation in an attempt to break or stop the tachyarrhythmia), the present invention modifies the device operation before the onset of the tachyarrhythmia with the intent of preemptively preventing such tachyarrhythmia from ever occurring. As indicated above, as a trigger for such preemptive action, the medical device may look for any specific spontaneous cardiac event, or sequence of events, that represent a marked departure from the patient's normal cardiac cycle. A sudden or marked departure from the patient's learned normal cardiac cycle, for example, may indicate that a tachyarrhythmia is likely to occur soon, e.g., within the next few minutes or the next several cardiac cycles. Hence, in response to detecting such a departure from the norm, the present invention immediately and automatically alters its basic operating algorithm (e.g., its pacing algorithm) so as to prevent the tachyarrhythmia from ever starting.

One technique used by the invention to define, or learn, the "normal" atrial and/or ventricular rhythm of the patient is to wait until the patient's cardiac rhythm is stable, and then capture the atrial and/or ventricular data defining such rhythm to form a template against which future atrial and/or ventricular events are compared. Such template may be formed either as a one-time occurrence, which is thereafter saved for future reference, or it may be continuously updated. In either event, marked abrupt changes from the "normal template" trigger the preemptive tachyarrhythmia pacing algorithm, which in turn initiate a specific change in the behavior of the medical device.

As another trigger for the preemptive action of the present invention, the pacemaker may optionally monitor one or more sensed physiological-based parameters of the patient, such as blood pressure, contractility, pre-ejection interval, intra-chamber impedance of the heart, stroke volume, or oxygen saturation, and trigger a selected preemptive tachyarrhythmia pacing algorithm or control scheme when there is a marked departure in such monitored parameter(s) from the norm, or when such monitored parameter(s) exceed a prescribed threshold.

It is thus a feature of the invention to provide an implantable pacemaker or defibrillator device which recognizes conditions suggestive of an upcoming tachyarrhythmia, which includes any undesirable cardiac rhythm or symptom, and (when such condition is identified) immediately takes action to alter the pacing mode or control mechanism of the implantable device in an attempt to pre-empt the occurrence of the tachyarrhythmia.

It is an additional feature of the invention, in accordance with one aspect thereof, to selectively provide overdrive pacing in an implantable pacemaker or defibrillator device as a means for preempting or preventing the occurrence of a tachyarrhythmia whenever monitored conditions suggest or indicate a tachyarrhythmia could soon occur.

It is a further feature of the invention, in accordance with another aspect thereof, to provide a prescribed or controlled amount of randomicity in the operation of an implantable medical device for the purpose of preempting the occurrence of a tachyarrhythmia or other cardiac disorder.

It is yet another feature of the invention, in accordance with still an additional aspect thereof, to utilize the increased memory capacity and processing capabilities of modern implantable medical devices, coupled with the use of appropriate implantable or other patient-coupled sensors, to recognize changes in the patient's physiology (and/or the patient's interaction with the implantable medical device) which are suggestive or indicative of an upcoming tachyarrhythmia.

BRIEF DESCRIPTION OF THE DRAWINGS AND APPENDIX

The above and other aspects, features and advantages of the present invention will be more apparent from the following more particular description thereof, presented in conjunction with the following drawings and appendix wherein:

FIG. 4 is a flowchart that illustrates in a general way how a preemptive tachyarrhythmia pacing control scheme may be invoked, applied, and terminated in accordance with the invention;

FIG. 5 shows a graph of the average hourly heart rate of eighteen patients as a function of time over a 24 hour period, and as such, illustrates a typical diurnal variation of the heart rate;

FIG. 6A illustrates a measured heart rate and sensed activity over a 24 hour period, and further shows a smoothed filtered signal obtained from such heart rate and/or activity signals when only a relatively long time constant is employed by the filter;

FIG. 8 is a flowchart that depicts how auto overdrive pacing is be achieved in accordance with one embodiment of the invention;

FIG. 9A is a simplified electrogram (EGM) timing diagram that illustrates auto overdrive pacing as achieved using the method depicted in FIG. 8;

FIG. 9B shows a representation of a canine EGM during which atrial auto overdrive pacing is employed;

FIG. 9C depicts the average heart rate versus time for the canine EGM trace of FIG. 9B;

FIG. 10 is a flowchart that illustrates pacing with randomicity in accordance with one embodiment of the invention.

Figure 1:
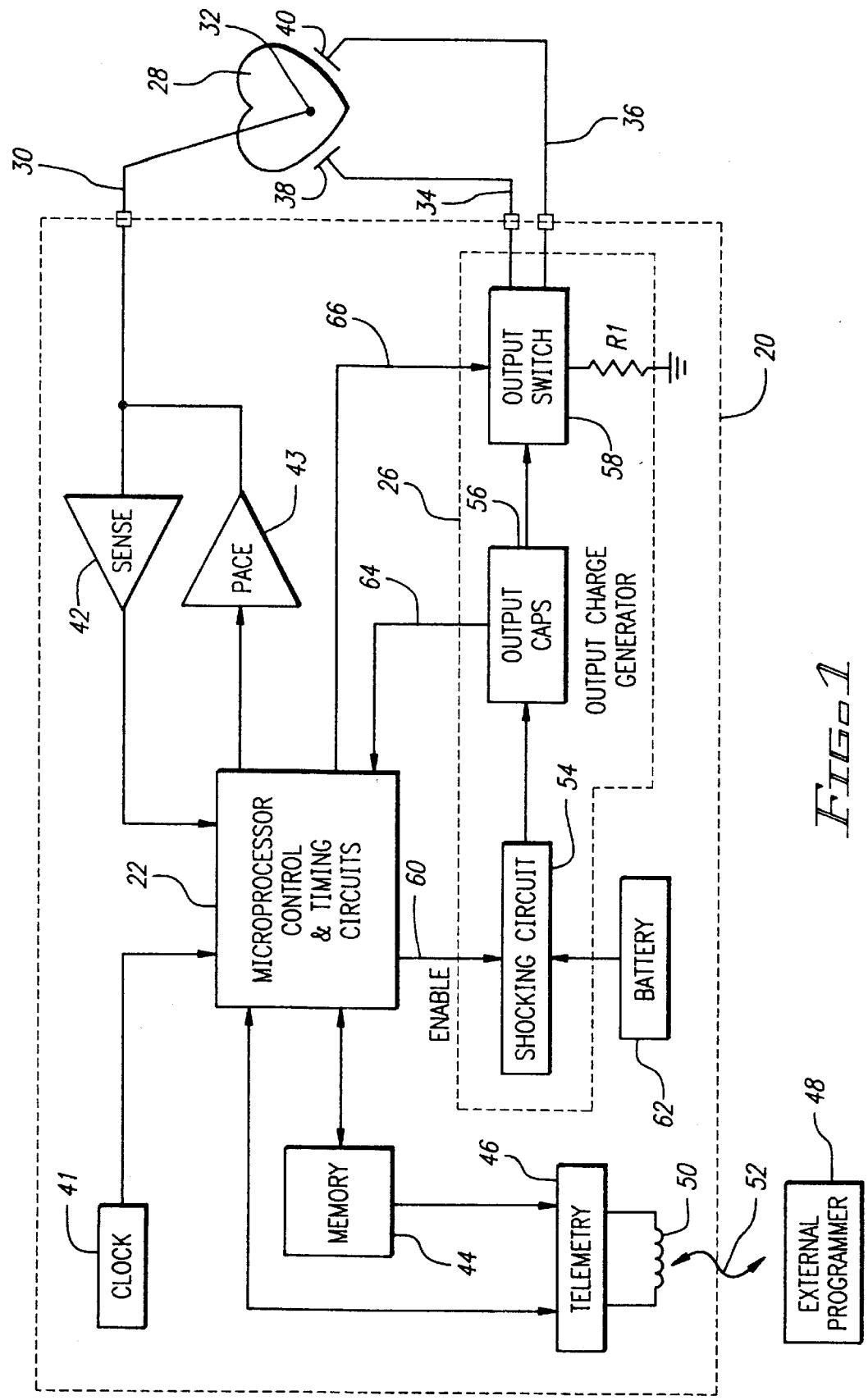
FIG. 1 shows a simplified functional block diagram of an implantable cardioverter-defibrillator (ICD), which represents one type of implantable medical device with which the present invention may be used.

Appendix A provides additional background information relative to pathologic tachyarrhythmias.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable medical devices, including an implantable cardioverter-defibrillator (ICD) or an implantable dual-chamber pacemaker or a combination thereof. To better understand the invention, it will first be helpful to have an understanding of the basic functions performed by the implantable medical device with which the invention is used, e.g., an ICD device and/or a dual-chamber pacemaker. To that end, reference is first made to FIG. 1, where there is shown a simplified functional block diagram of an ICD device 20, and to FIG. 2, where there is shown a simplified functional block diagram of a dual-chamber pacemaker 70. It should also be noted that in some instances the functions of an ICD and a pacemaker may be combined within the same medical device. However, for purposes of the explanations that follow, it is assumed that separate medical devices are used for each function.

It is the primary function of an ICD device to sense the occurrence of an arrhythmia, and to automatically apply an appropriate sequence of stimulation pulses (antitachycardia pacing) or an electrical shock therapy to the heart aimed at terminating the arrhythmia. To this end, the ICD device 20, as shown in the functional block diagram of FIG. 1, includes a microprocessor-based control and timing circuit 22 (hereafter a "control/timing" circuit 22) that controls an output charge generator 26. The output charge generator 26 generates output electrical stimulation pulses of low, moderate or high energy (tachycardia, cardioversion or defibrillation pulses) (e.g., electrical pulses having energies of from 0.5–25 microjoules (low); 1–10 joules (moderate); or 11–40 joules (high)), as controlled by the control/timing circuit 22. Such moderate or high energy pulses are applied to the patient's heart through at least two leads 34 and 36, each of which is respectively coupled to a suitable implanted electrode 38 or 40 positioned to be in contact with the heart 28. While the electrodes 38 and 40 are shown as patch electrodes that are placed in contact with, or near, external cardiac tissue, they may also be of the endocardial type which incorporate both pacing and shocking electrodes on a single lead. The electrodes 38 and 40 may be of conventional design, and may be implanted using known techniques. It is to be understood that additional defibrillation leads (e.g., a subcutaneous lead) may be used as desired or needed in order to efficiently and effectively apply the shock treatment generated by the high voltage generator 26 to the patient's heart 28.

The ICD 20 also includes a sense amplifier 42 that is coupled to sensing lead 30 and electrode 32. It is the function of the sense amplifier 42 to sense the activity of the heart 28 as manifest by the presence of certain electrical signals sensed through the electrode 32. That is, as is known in the art, R-waves occur upon the depolarization, and hence contraction, of ventricular tissue; and P-waves occur upon the depolarization, and hence contraction, of atrial tissue. Thus by sensing R-waves and/or P-waves through the sense amplifier 42, and providing such sensed signals to the control/timing circuit 22, the control/timing circuit 22 is able to make a determination as to the rate and regularity of the patient's heart beat. Such information, in turn, allows the control/timing circuit 22 to determine whether the heart 28 of a patient is experiencing an arrhythmia.

The control/timing circuit 22 further has a memory circuit 44 coupled thereto wherein the operating parameters used by the control/timing circuit 22 are stored. Such operating parameters define, for example, the amplitude of each shock energy pulse to be delivered to the patient's heart 28 within each tier of therapy, as well as the duration of these shock pulses. The memory 44 may take many forms, and may be subdivided into as many different memory blocks or sections (addresses) as needed to store desired data and control information. A feature of the present invention, in some embodiments thereof, is the ability to sense and store a relatively large amount of data as a data record, which data record may then be used to guide the operation of the device, i.e., the present operating mode of the device may be dependant, at least in part, on past performance data.

Advantageously, the operating parameters of the implantable device 20 may be noninvasively programmed into the memory 44 through a telemetry circuit 46, in telecommunicative contact with an external programmer 48 by way of a suitable coupling coil 50. The coupling coil 50 may serve as an antenna for establishing a radio frequency (rf) communication link 52 with the external programmer 48; or the coil 50 may serve as a means for inductively coupling data to and from the telemetry circuit 46 from and to the external programmer 48, as is known in the art. Further, such telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that carries out the functions described herein. The use, design, and operation of microprocessor-based control circuits to perform timing and data analysis functions is known in the art.

Figure 2:
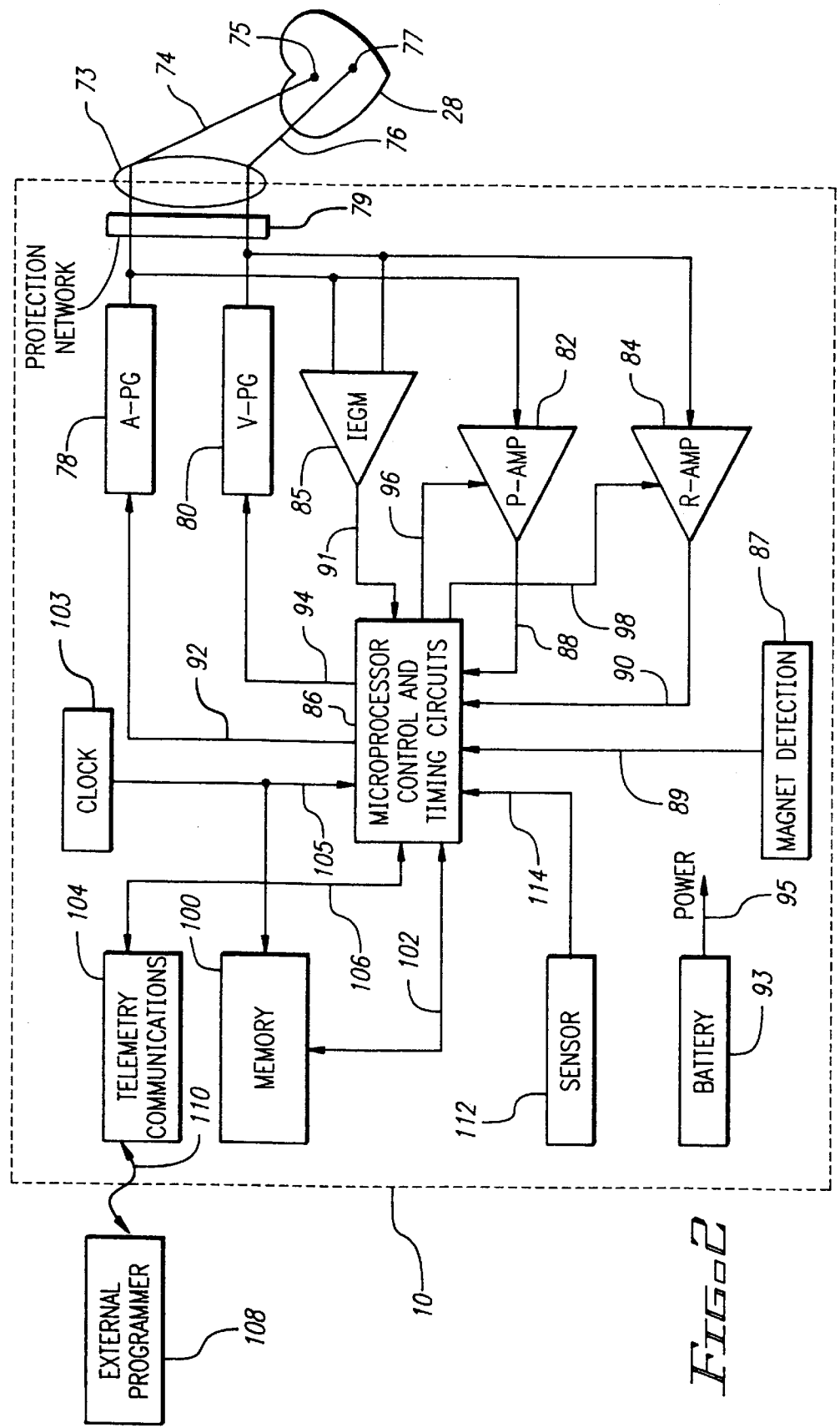
FIG. 2 shows a functional block diagram of an implantable, programmable, dual-chamber pacemaker, which represents another type of implantable medical device with which the invention may be used.

Referring next to FIG. 2, a simplified block diagram of the dual-chamber pacemaker 70 is illustrated. The pacemaker 70 is coupled to a heart 28 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 70 through a connector 73 that forms an integral part of the housing wherein the circuits of the pacemaker are housed.

The connector 73 is electrically connected to a protection network 77, which network 77 electrically protects the circuits within the pacemaker 10 from excessive shocks or voltages that could appear on the electrodes 75 and/or 77 in the event such electrodes were to come in contact with a high voltage signal, e.g., from a defibrillator shock.

The leads 74 and 76 carry stimulating pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (P-AMP) 82; and electrical signals from the ventricles are carried from the electrode 77, through the lead 76, to the input terminal of a ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture". (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.)

The dual-chamber pacemaker 70 is controlled by a control system 86 that typically includes a microprocessor programmed to carry out control and timing functions. The control system 86 receives the output signals from the atrial (P-AMP) amplifier 82 over signal line 88. Similarly, the control system 86 receives the output signals from the ventricular (R-AMP) amplifier 84 over signal line 90, and the output signals from the IEGM amplifier 85 over signal line 91. These output signals are generated each time that a P-wave or an R-wave or an evoked response is sensed within the heart 28. The control system 86 also generates trigger signals that are sent to the atrial pulse generator (A-PG) 78 and the ventricular pulse generator (V-PG) 80 over signal lines 92 and 94, respectively. These trigger signals are generated each time that a stimulation pulse is to be generated by the respective pulse generator 78 or 80. The atrial trigger signal is referred to simply as the "A-trigger", and the ventricular trigger signal is referred to as the "V-trigger". During the time that either an A-pulse or V-pulse is being delivered to the heart, the corresponding amplifier, P-AMP 82 and/or R-AMP 84, is typically disabled by way of a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action, if followed by a refractory period, also helps prevent residual electrical signals present in the muscle tissue as a result of the pacemaker stimulation from being interpreted as P-waves or R-waves.

The pacemaker 70 also includes a memory circuit 100 that is coupled to the control system 86 over a suitable data/address bus 102. This memory circuit 100 allows certain control parameters, used by the control system 86 in controlling the operation of the pacemaker, to be programmably stored and modified, as required, in order to customize the pacer's operation to suit the needs of a particular patient. Further, data sensed during the operation of the pacemaker may be stored in the memory 100 for later retrieval and analysis.

As with the memory 44 of the ICD device 20 (shown in FIG. 1), the memory 100 of the pacemaker 70 in FIG. 2 may take many forms, and may be subdivided into as many different memory blocks or sections (addresses) as needed in order to allow desired data and control information to be stored. A feature of the present invention, in some embodiments thereof, is the ability to store a relatively large amount of sensed data as a data record, which data record may then be used to guide the operation of the device. That is, the operating mode of the pacemaker may be dependant, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently-sensed parameters. Advantageously, modern memory devices allow for the storage of large amounts of data in this manner.

A clock circuit 103 directs an appropriate clock signal(s) to the control system 86, as well as to any other needed circuits throughout the pacemaker 70 (e.g., to the memory 100) by way of clock bus 105.

A telemetry/communications circuit 104 is further included in the pacemaker 70. This telemetry circuit 104 is connected to the control system 86 by way of a suitable command/data bus 106. In turn, the telemetry circuit 104, which is included within the implantable pacemaker 70, may be selectively coupled to an external programming device 108 by means of an appropriate communication link 110, which communication link 110 may be any suitable electromagnetic link, such as an RF (radio frequency) channel, a magnetic link, an inductive link, an optical link, and the like. Advantageously, through the external programmer 108 and the communication link 110, desired commands may be sent to the control system 86. Similarly, through this communication link 110 with the programmer 108, data commands (either held within the control system 86, as in a data latch, or stored within the memory 100) may be remotely received from the programmer 108. Similarly, data initially sensed through the leads 74 or 76, and processed by the microprocessor control circuits 86, or other data measured within or by the pacemaker 70, may be stored and uploaded to the programmer 108. In this manner, noninvasive communications can be established with the implanted pacemaker 70 from a remote, non-implanted, location.

The pacemaker 70 additionally includes a battery 93 which provides operating power to all of the circuits of the pacemaker 70 via a POWER signal line 95.

It is noted that the pacemaker 70 in FIG. 2 is referred to as a dual-chamber pacemaker because it interfaces with both the atria and the ventricles of the heart. Those portions of the pacemaker 70 that interface with the atria (e.g., the lead 74, the P-wave sense amplifier 82, the A-PG 78, and corresponding portions of the control system 86) are commonly referred to as the "atrial channel". Similarly, those portions of the pacemaker 70 that interface with the ventricles (e.g., the lead 76, the R-wave sense amplifier 84, the V-pulse generator 80, and corresponding portions of the control system 86) are commonly referred to as the "ventricular channel".

As needed for certain applications, the pacemaker 70 may further include at least one sensor 112 that is connected to the control system 86 of the pacemaker 70 over a suitable connection line 114. While this sensor 112 is illustrated in FIG. 2 as being included within the pacemaker 70, it is to be understood that the sensor may also be external to the pacemaker 70, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" pacemakers in order to adjust the rate (pacing cycle) of the pacemaker in a manner that tracks the physiological or metabolic needs of the patient.

The pacemaker 10 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 70, and/or to signal the control system 86 that an external programmer 108 is in place to receive data from, or send data to, the pacemaker memory 100 or control system 86 through the telemetry communications circuits 104.

As with the ICD device 20 of FIG. 1, the telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which all of these pacing elements cooperate with each other in order to provide a particular pacing mode of operation. Such cooperation is controlled by the control system 86.

The control system 86 may be realized using a variety of different techniques and/or circuits. The preferred type of control system 86 is a microprocessor-based control system. It is noted, however, that the control system 86 could also be realized using a state machine. Indeed, any type of control circuit or system could be employed for the control system 86. The present invention is likewise not concerned with the details of the control system 26. Rather, it is concerned with the end result achieved by the control system. That is, so long as the control system 86 controls the operation of the pacemaker (or other medical device) so that the desired functions are achieved as set forth herein (e.g., by following the steps described below in the flowchart of FIG. 4), it matters little what type of control system is used. Those of skill in the implantable medical device art, given the teachings presented herein, should thus be able to fashion numerous different types of control systems or circuits that achieve the desired device control.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment." Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their interrelationship are more thoroughly described. The '052, '555, '298 and '980 patents are incorporated herein by reference.

Because various types of control systems 26 may be used with the invention, it is convenient to describe the present invention in terms of a "function tree" as well as a high-level flowchart that illustrates, in a broad sense, what it is that the ICD 20 or pacemaker 70 used with the invention does to achieve preemptive tachyarrhythmia pacing, and when such preemptive tachyarrhythmia pacing is invoked. Hence, reference is next made to FIG. 3, which shows a function tree of the invention, which function tree provides a non-exhaustive list of the various types of preemptive tachyarrhythmia pacing schemes that may be implemented by the invention.

Figure 3:
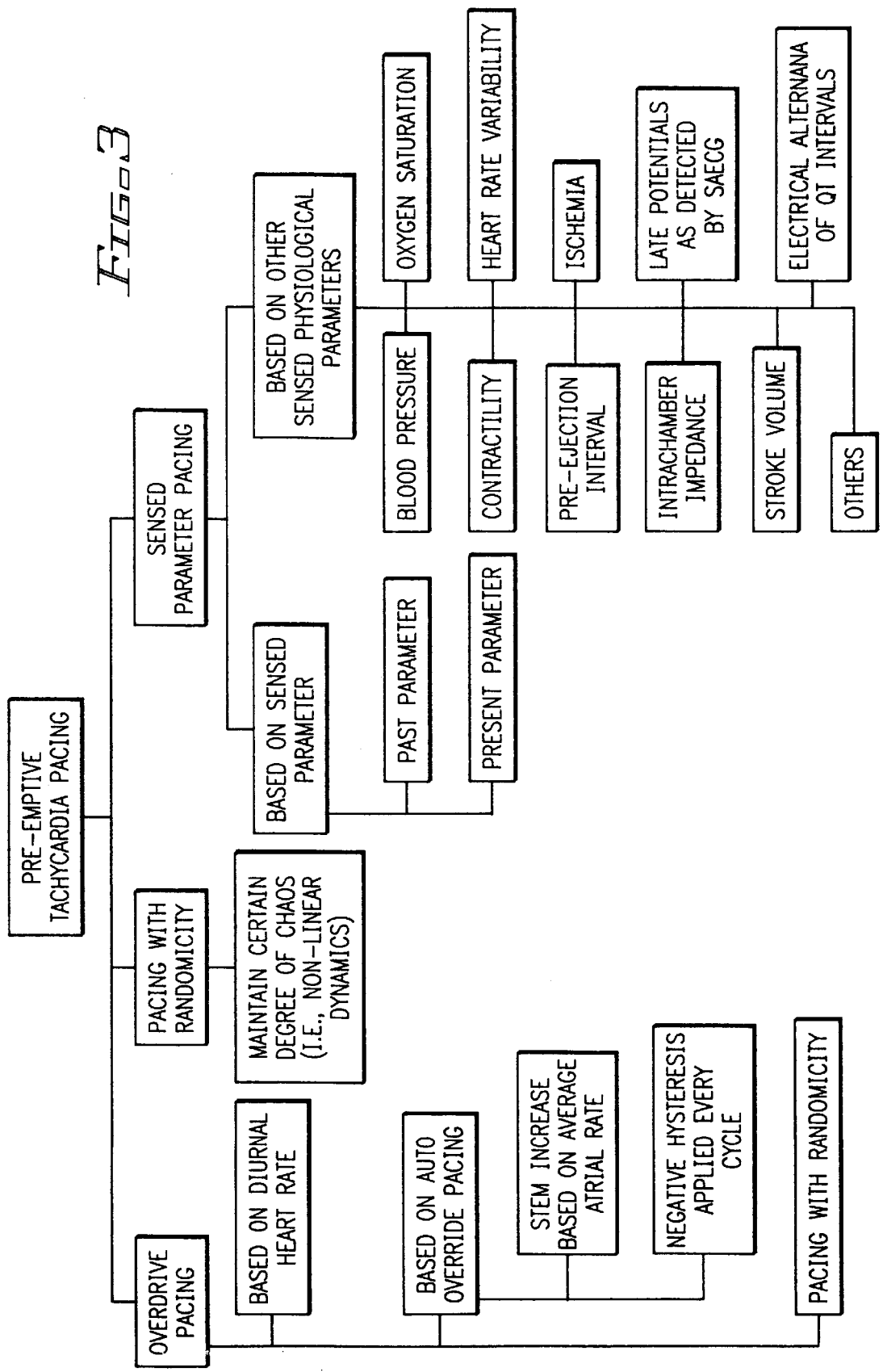
FIG. 3 shows the various types of preemptive tachyarrhythmia pacing control schemes (or PTP algorithms) that may be implemented or used by the invention, which list is sometimes referred to herein as a "function tree"

As seen in FIG. 3, there are three broad types of preemptive tachyarrhythmia pacing schemes contemplated by the invention. A first scheme may be broadly described as "overdrive pacing", a second scheme may be described as "pacing with randomicity", and a third scheme may be described as "sensed parameter pacing." Each of these pacing schemes is described in more detail below. It should be noted, however, that these different pacing schemes are not necessarily mutually exclusive. Rather, certain features of the different preemptive tachyarrhythmia pacing schemes may be combined. For example, automatic atrial overdrive pacing may be employed with pacemaker-induced random pacing intervals—a form of randomicity—in order to modify atrial tissue refractory times.

As also seen in FIG. 3, overdrive pacing may be achieved using alternate approaches, including: (1) Overdrive Pacing based on diurnal heart rate; and (2) Automatic Atrial Overdrive Pacing. Automatic atrial overdrive pacing, in turn, may be achieved using various approaches, including: (a) a step increase or change in atrial rate based on average atrial rate; and/or (b) negative hysteresis applied, e.g., during each cardiac cycle. Similarly, FIG. 3 shows that pacing based on sensed parameters may be based on either a past or present sensed parameter, such as atrial rate, or on other sensed physical or physiological parameters. Such parameters may include, e.g., blood pressure, heart contractility, pre-ejection interval, cardiac intra-chamber impedance, stroke volume, or blood oxygen saturation.

The various preemptive tachyarrhythmia pacing (PTP) functions shown in the function tree of FIG. 3 are typically carried out, or invoked, as illustrated in the basic flowchart depicted in FIG. 4. Those of skill in the art will readily appreciate that the flowchart shown in FIG. 4 is only exemplary, and that the basic functions listed in FIG. 3 could be achieved using processes or steps other than those shown in FIG. 4.

It should further be noted that the method shown in FIG. 4, and that which is to be described next, is a general method that may be used with any of the preemptive tachyarrhythmia pacing techniques described herein (e.g., any one of the functions identified in FIG. 3). Hence, the method of FIG. 4 will first be described in general terms. Specific examples of how the method applies to particular ones of the preemptive tachyarrhythmia pacing techniques listed in FIG. 3 will be presented later.

As shown in FIG. 4, it is seen that a first step of the method is to initialize the device (block 118), which device could be, e.g., a pacemaker, an ICD device, or other stimulating device. Such initialization typically occurs by loading and/or programming the basic operating parameters, commands and/or data needed to operate the device. Next, a decision is made (block 120) as to whether preemptive tachyarrhythmia pacing is to continue. This decision is made as a means of terminating the method if preemptive tachyarrhythmia pacing is not to continue (NO branch of block 120). If preemptive tachyarrhytmia pacing is to continue (YES branch of block 120), then a selection or decision is made as to whether the device is to be operated in a "continuous" or "non-continuous" preemptive tachyarrhythmia pacing mode (block 122). In a continuous preemptive tachyarrhythmia pacing mode, the device continually checks (e.g., every cardiac cycle) for conditions indicative of a need for preemptive tachyarrhythmia pacing, or continually applies (e.g., every cardiac cycle or every 2d or 3d cardiac cycle) a pacing regime aimed at preventing a tachyarrhythmia. In a non-continuous preemptive tachyarrhythmia pacing mode, preemptive tachyarrhythmia pacing is applied only when triggered, e.g., only after certain monitored data or conditions suggest that preemptive tachyarrhythmia pacing would be appropriate.

When a continuous preemptive tachyarrhythmia pacing mode is selected (YES branch of block 122), the desired preemptive tachyarrhythmia pacing algorithm for use with the continuous preemptive tachyarrhythmia pacing mode (e.g., a selected type of overdrive pacing) is selected and loaded into the appropriate location of the device memory (block 124). The device is then operated in accordance with the selected preemptive tachyarrhythmia pacing algorithm (block 126). During such operation, periodic and/or user-invoked inquiries are made to determine if a new preemptive tachyarrhythmia pacing algorithm should be selected (block 128). If so (YES branch of block 128), then the new preemptive tachyarrhythmia pacing algorithm is loaded into the appropriate location of the device memory (block 124), and the device continually operates in accordance with the newly-selected preemptive tachyarrhythmia pacing algorithm (block 126). If a new preemptive tachyarrhythmia pacing algorithm is not selected (NO branch of block 128), then a further determination is made as to whether preemptive tachyarrhythmia pacing operation of the device should continue in the previously-selected continuous preemptive tachyarrhythmia pacing mode (block 130). If operation is to continue in the continuous preemptive tachyarrhythmia pacing mode (YES branch of block 130), then the device continues to be operated in accordance with such previously-selected preemptive tachyarrhythmia pacing mode (block 126). If operation is not to continue in the continuous preemptive tachyarrhythmia pacing mode (NO branch of block 130), then a further determination is made as to whether preemptive tachyarrhythmia pacing is to continue (block 120). If not (NO branch of block 120), then preemptive tachyarrhythmia pacing operation ceases. If so (YES branch of block 120), then another opportunity is presented to select either continuous or non-continuous preemptive tachyarrhythmia pacing operation (block 122).

When a non-continuous preemptive tachyarrhythmia pacing is selected (NO branch of block 122), then the desired preemptive tachyarrhythmia pacing algorithm is selected and/or loaded in the appropriate memory location of the device (block 132). Generally, a non-continuous preemptive tachyarrhythmia pacing operation comprises some type of a sampled system, wherein one or more sets of data are gathered and compared to a baseline data set. Thus, any sensors that may need to be enabled in order to gather the needed baseline data, and/or to gather subsequent data, are enabled (block 134). The baseline data corresponding to the selected preemptive tachyarrhythmia pacing algorithm, if not included as part of the initialization data (e.g., at block 118), is then gathered (block 136). Such baseline data is thereafter used as a reference against which subsequent sensed/gathered data is compared. Hence, once the baseline data has been obtained, then appropriate thresholds are set for triggering the selected preemptive tachyarrhythmia pacing algorithm (block 138). Generally, such thresholds may be simply the baseline value, or a prescribed multiple of the baseline value. For example, if the baseline data set is "x", and if "x" is set as the threshold, and if a subsequent data set is "y", and if "y" is greater than "x", then the fact that "y" is greater than "x" means that the threshold has been exceeded, which in turn means that the selected preemptive tachyarrhythmia pacing algorithm will be triggered. In other situations, the threshold may be set to some factor greater than the baseline, e.g., two times "x" (2x) or three times "x" (3x). In such situations, the preemptive tachyarrhythmia pacing algorithm would only be triggered if a subsequent data set "y" is greater than 2x or 3x, respectively.

Once the appropriate threshold(s) have been set for the selected Preemptive tachyarrhythmia pacing algorithm, the device is operated in its programmed mode (block 140). As the device is thus operated, the patient is monitored through the appropriate sensor(s) in order to gather a data set which can be compared against the baseline data set (block 142). As each data set is gathered, a decision is made as to whether the monitored data set exceeds the trigger threshold(s) (block 144). If not (NO branch of block 144), then device operation continues in the selected mode and the process repeats (blocks 140, 142, 144). If the trigger threshold(s) is exceeded (YES branch of block 144), then the selected preemptive tachyarrhythmia pacing algorithm (e.g., overdrive pacing) is invoked (block 146), and the device is operated in accordance with the selected preemptive tachyarrhythmia pacing algorithm (block 148).

The device continues to be operated in the triggered preemptive tachyarrhythmia pacing algorithm for a prescribed period of time (e.g., for a specified number of cardiac cycles or for a prescribed time period in terms of minutes or hours or until a prescribed event occurs). Thus, as the device is operated in accordance with the triggered preemptive tachyarrhythmia pacing algorithm (block 148), a determination is regularly made as to whether the triggered preemptive tachyarrhythmia pacing algorithm should continue to be used (block 150), i.e., a determination is made as to whether the preemptive tachyarrhythmia pacing algorithm has been used long enough to achieve its desired goal of reducing the likelihood of a tachyarrhythmia from occurring. If the preemptive tachyarrhythmia pacing algorithm has not been used sufficiently long (NO branch of block 150), then the device continues to operate in accordance with such triggered preemptive tachyarrhythmia pacing algorithm. If the preemptive tachyarrhythmia pacing algorithm has been used sufficiently long (YES branch of block 150), then the monitored parameters or sensor outputs are rechecked (block 152), i.e., a new data set is obtained and compared to the trigger threshold(s) (block 154) to see if the conditions which triggered the need for the preemptive tachyarrhythmia pacing algorithm in the first place still persist. If the new data set remains greater than the trigger threshold(s) (YES branch of block 154), then the device continues to operate in accordance with the selected preemptive tachyarrhythmia pacing algorithm (block 148), and the process repeats (blocks 150, 152, 154). If the new data set is less than the trigger threshold(s) (NO branch of block 154), then that suggests the preemptive tachyarrhythmia pacing algorithm is no longer needed.

Thus, it is seen that the preemptive tachyarrhythmia pacing control algorithm, when invoked, modifies the behavior of the implantable medical device for the purpose of preventing a tachyarrhythmia. After being triggered (i.e., when not invoked on a continuous basis), the preemptive tachyarrhythmia pacing algorithm continues to control the medical device to preemptively prevent the occurrence of a tachyarrhythmia until: (a) a programmed period of time has elapsed, (b) a programmed number of events have occurred, (c) certain monitored performance criteria are achieved, or (d) the apparent or perceived danger of a tachyarrhythmia has subsided or otherwise passed.

If the preemptive tachyarrhythmia pacing algorithm is no longer needed, based on a comparison of the new data set with the trigger threshold(s), as performed at blocks 152, 154, then a determination may be made as to whether the same or a new preemptive tachyarrhythmia pacing algorithm should be invoked the next time a preemptive tachyarrhythmia pacing algorithm is needed (block 156). If the same preemptive tachyarrhythmia pacing algorithm is to continue to be used (NO branch of block 156), then the device is operated in accordance with its programmed mode (beginning at block 140 and continuing through blocks 142–154). If a different preemptive tachyarrhythmia pacing algorithm is desired (YES branch of block 156), and if non-continuous preemptive tachyarrhythmia pacing operation is to continue (YES branch of block 158), then the operating parameters associated with the desired preemptive tachyarrhythmia pacing algorithm are loaded into the appropriate location of the device memory (block 132), the appropriate sensor(s) needed with the new/different preemptive tachyarrhythmia pacing algorithm are enabled (block 134), and the process continues (blocks 136 et seq.) as described previously.

With the above generalized method of performing preemptive tachyarrhythmia pacing (PTP) in mind, a more detailed description of some of the PTP techniques and methods of the present invention, and the manner in which such are integrated with FIG. 4, are next presented.

Overdrive Pacing

An important preemptive tachyarrhythmia pacing technique that may be used with the present invention is overdrive pacing. By "overdrive pacing" it is meant a pacing scheme or technique wherein a stimulation pulse is always applied to the appropriate heart chamber, e.g., the atrium, at a time in the pacing cycle which will most always be prior to a natural depolarization. Hence, overdrive pacing involves pacing the heart at a rate that is just slightly faster than what the heart's own natural rate would be.

Overdrive pacing in accordance with the present invention, as seen in the function tree of FIG. 3, may be: (a) based on a diurnal rate; (b) automatically invoked based on either: (1) a step increase over the average atrial rate, or (2) negative hysteresis applied every cycle; and/or (c) performed with randomicity. Each of these overdrive pacing approaches is described more fully below.

a. Overdrive Pacing Based on Diurnal Rate

A first technique or approach for applying overdrive pacing is based on a measured and/or programmed diurnal rate. The use of a diurnal rate to adjust the base rate of a pacemaker is described in Bornzin et al., "Adjusting Heart Rate During Sleep Using Activity Variance", *PACE*, Vol. 17, (Pt. II) pp. 1933–1938 (November 1994), incorporated herein by reference. See also U.S. Pat. No. 5,476,483 (Bornzin et al.), and commonly-owned U.S. patent application Ser. No. 08/255,194, filed Jun. 7, 1994, both of which documents are likewise incorporated herein by reference. As taught in the cited references, the heart rate of a typical patient, as well as numerous other physiological processes and parameters (e.g., blood pressure, temperature, endogenous corticosteroids, etc.) demonstrate a rhythmic variation during the day. This variation is termed the circadian or "diurnal" variation (and is frequently referred to herein as the diurnal rate). In accordance with this diurnal variation, the heart rate typically reaches its highest peak during the day, when the patient is awake and active, and drops to its lowest rate or resting rate during the early morning hours when most people are usually asleep. A typical diurnal variation, depicted as an average hourly minimum heart rate and an average hourly heart rate of eighteen patients as a function of time (e.g., over a 24-hour day) is illustrated in FIG. 5.

The basic premise addressed in the cited references is to determine the diurnal rate of a given patient and then set the "base rate" of the patient's pacemaker to a value that is a function of the diurnal rate (e.g., to a value that is a prescribed value less than the determined diurnal rate) when the patient is sleeping. The base rate of a pacemaker is that rate below which the natural heart rate may not fall without having the pacemaker step in with a pacing pulse. As such, the base rate effectively defines a minimum heart rate for the patient. Thus, by modulating the base rate as a function of the diurnal rate, the base rate tracks or follows the diurnal rate when the patient is asleep or inactive. As a result, the base rate of the pacemaker need not be a fixed rate (e.g., 60 bpm), but may assume various values (e.g., from 50 to 60 bpm) at those times when the patient is asleep or inactive.

The present invention adopts and expands upon the basic premise of the cited references and determines an appropriate diurnal variation for the patient. Such diurnal variation is then used to determine an appropriate diurnal base rate for the patient as a function of time of the day which will, for the most part (e.g., during most cardiac cycles), assure overdrive pacing. For example, if the diurnal variation indicates a heart rate, for a given time of the day, of 60 bpm (beats per minute), corresponding to a cardiac pacing interval of 1000 milliseconds (ms), then the present invention sets the diurnal base rate at something less than 1000 ms (e.g., 950 ms) corresponding to a pacing rate of approximately 63 ppm.

A key aspect of the above-described approach is the manner in which the diurnal variation and the diurnal base rate are determined. Various methods exist for determining the diurnal variation and corresponding diurnal base rate, including the methods taught in U.S. Pat. No. 5,476,483, previously referenced and incorporated herein by reference. In particular, a preferred way to determine the diurnal base rate is patterned after the "third approach" described in U.S. Pat. No. 5,476,483, e.g., at col. 7, lines 38–60; or the "third embodiment" described at col. 18, line 9, through col. 20, line 38; and in FIG. 9 of U.S. Pat. No. 5,476,483 patent. Basically, this approach involves iteratively calculating the diurnal base rate as a function of a running average of the sensed heart rate, or (if a sensed heart rate signal is not available, e.g., as in the case of a diseased or defective heart that must be paced) a running average of an activity signal representative of what a natural heart rate signal would be.

More particularly, in accordance with a preferred iterative process, the average heart rate signal (and/or the activity signal) s digitally filtered using both a relatively short time constant (e.g., about 1.6 minutes) and a relatively long time constant (e.g., about 38 minutes). The longer time constant results in components of the filtered heart rate signal that are resistant to short-term fluctuations in the heart rate (or activity), thereby yielding a stable average pacing rate that gradually transitions over time. In contrast, the shorter time constant results in components of the filtered heart rate signal (or activity signal) that are somewhat more responsive to short-term variations, thereby allowing for components of the average heart rate signal that reflect the more rapid fluctuations of the heart rate.

Figure 6B:
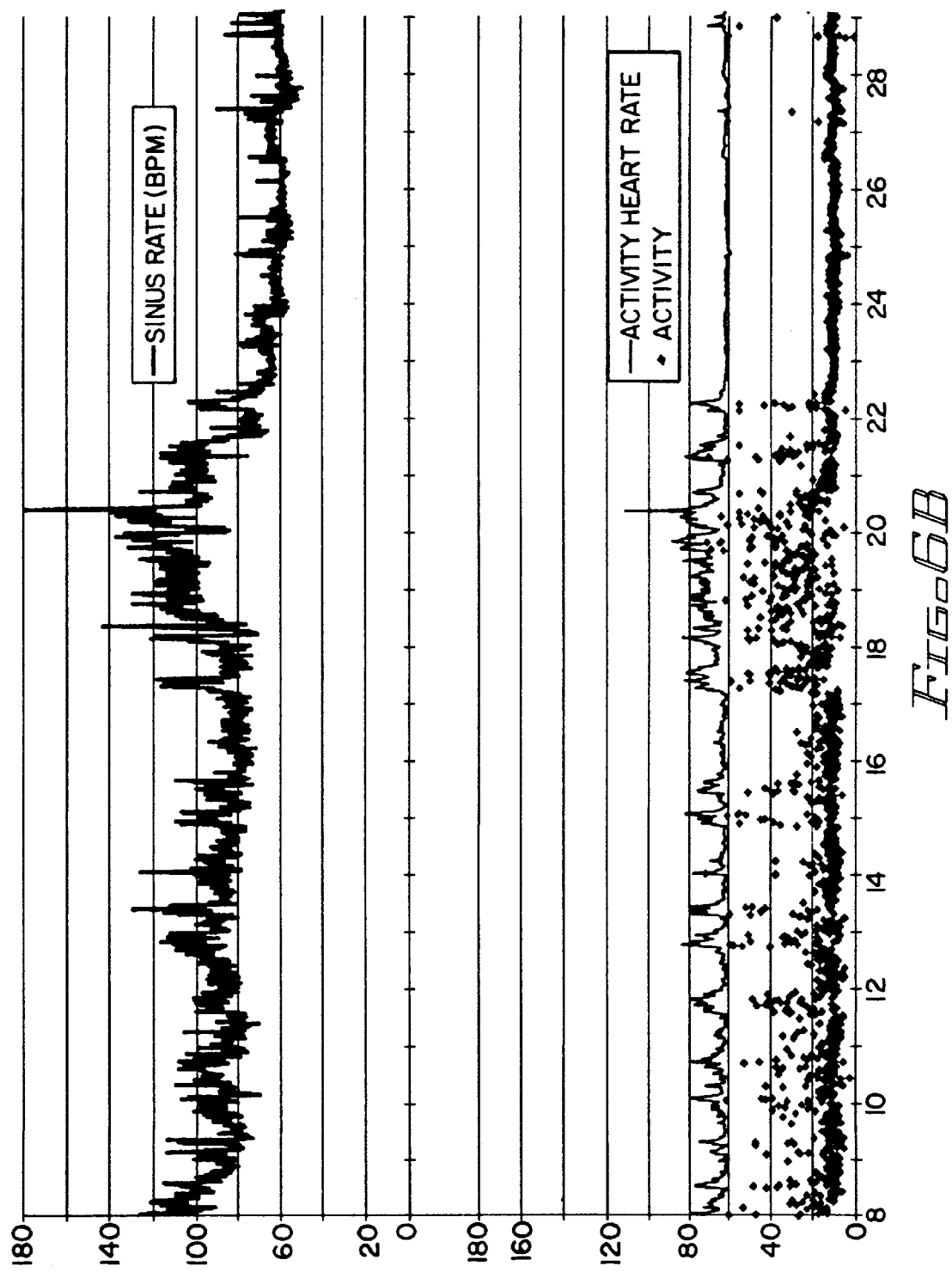
FIG. 6B is the same as FIG. 6A, except that only a relatively short time constant is employed by the filter.
Figure 6C:
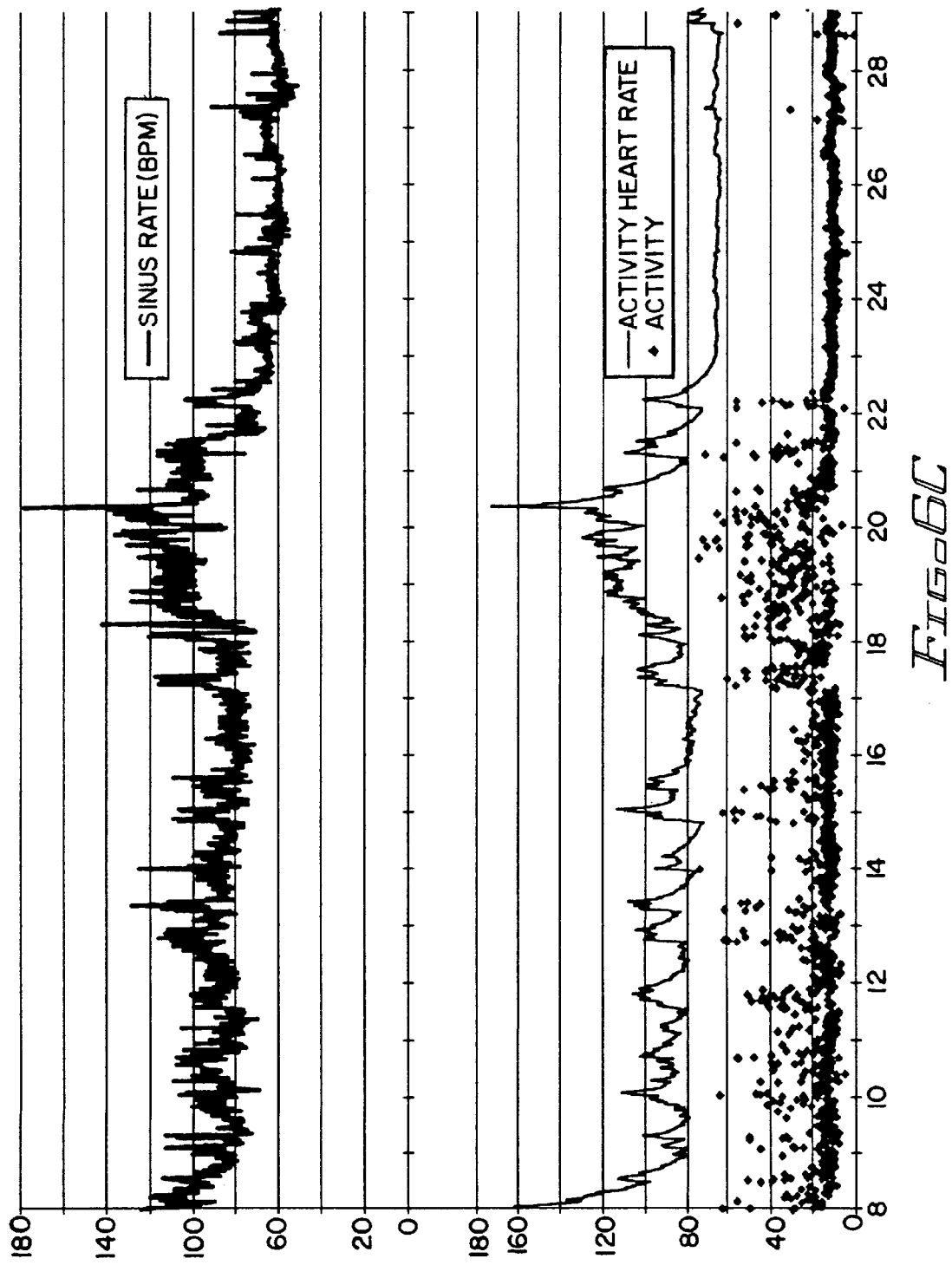
FIG. 6C is the same as FIG. 6A, except that both the relatively long and short time constants are employed by the filter.

The above concept (of filtering with both a relatively long time constant and a relatively short time constant) is further illustrated in FIGS. 6A, 6B and 6C. In these figures, the rate, in events/minute (e.g., bpm), is shown along the vertical axis, and time is shown along the horizontal axis. FIG. 6A illustrates the filtering of a rapidly changing heart rate signal 162 and an activity signal (represented by the diamond-shaped dots 164) when only a relatively long time constant, e.g., 38 minutes, is used. As seen in FIG. 6A, a relatively smooth and staple average heart rate signal 160 results. In contrast, FIG. 6B shows the filtering of the same rapidly-changing heart rate signal 162 and activity signal 164 when using only a relatively short time constant, e.g., 1.6 minutes. As seen in FIG. 6B, an average signal 166 results which, although smoothed, varies or follows the more rapid variations of the heart rate signal 162, but does not follow the slower variations of the heart rate signal. Finally, FIG. 6C shows the filtering of the same rapidly-changing heart rate signal 162 and activity signal 164 when using both the long (e.g., 38 minutes) and short (e.g., 1.6 minute) time constants. As seen in FIG. 6C, the resulting filtered signal 168 comprises a smoothed signal that includes both the long term and short term variations of the heart rate signal.

In accordance with the present invention, the filtered signal obtained using the relatively long time constant (e.g., the signal 160 in FIG. 6A) provides a signal that may be used as the diurnal base rate signal; whereas the filtered signal 163 obtained using both the short and long time constants may be used as the sensor-indicated rate (SIR) signal for the pacemaker.

While various techniques and methods may be used to perform the digital filtering using long and short time constants as described above, the preferred approach applies first and second recursive, low-pass digital filters to the detected difference (or change) in the heart rate average (and/or activity average) over respective first and second delays (or sampling times). These differences, DIFF(t), are then processed using low pass, first order, recursive digital filters, as explained below.

The preferred interative approach used in accordance with this aspect of the invention may be described by the following relationships:

$$DIFF1(t) = |Lastav(t) - Lastav(t - delay1)| \quad (1)$$

$$CT\_SD1(t) = \frac{1}{k}DIFF1(t) + \frac{k-1}{k}ACT\_SD1(t - delay1) \quad (2)$$

$$DIFF2(t) = |Lastav(t) - Lastav(t - delay2)| \quad (3)$$

$$CT\_SD2(t) = \frac{1}{j}DIFF1(t) + \frac{j-1}{j}ACT\_SD2(t - delay1) \quad (4)$$

$$DBR = Slope2 \cdot [ACT\_SD2(t)] + Sleeprate \quad (5)$$

$$SIR = Slope1 \cdot [ACT\_SD1(t)] + DBR \quad (6)$$

With reference to the above equations, Eq. (1) is first used to determine a first difference, DIFF1(t), between the most recently-determined average heart rate, Lastav(t), and the prior most recently-determined average heart rate, Lastav(t-Delay1), where "Delay1" is a specified time delay between when the most recent average heart rate was determined, and the prior most recent average heart rate was determined. Typically, "Delay1" will be specified as a prescribed number of cardiac cycles (e.g., n1 cardiac cycles), where n1 is an integer of from 1 to 32 (e.g., 1 cardiac cycle). Alternatively, "Delay1" could be specified as a time increment (e.g., m1 seconds), where m1 may vary from 1 to 30 seconds.

Once "DIFF1(t)" has been determined, then an effective time constant associated with the first recursive filter, "ACT_SD1(t)", is determined using Eq. (2) based on a specified constant k, the most recent value of "DIFF1(t)", and the prior most recent value of the effective time constant of the first filter, ACT_SD1(t-Delay1). The value of k is determined empirically, but is usually a relatively high value, on the order of 100–200 (e.g., 128).

In a similar manner, Eq. (3) is used to determine a second difference, DIFF2(t), between the most recently-determined average heart rate, Lastav(t), and a prior most recently-determined average heart rate, Lastav(t-Delay2), where "Delay2" is a second specified delay between when the most recent average heart rate was determined and a prior most recent average heart rate was determined. In the preferred embodiment, "Delay2" is longer than "Delay1", and is usually specified as a time increment, e.g., m2 seconds, where m2 may vary from, e.g, 15 to 60 seconds, preferably 26 seconds. Alternatively, "Delay2" could be specified as a number of cardiac cycles, e.g., n2 cycles, where n2 may vary from, e.g., 10 to 100.

Once "DIFF2(t)" has been determined, then an effective time constant associated with the second recursive filter, "ACT_SD2(t)", is determined using Eq. (4) based on a specified constant j, the most recent value of "DIFF2(t)", and the prior most recent value of the effective time constant of the second filter, ACT_SD2(t-Delay2). The value of j is determined empirically, but is usually a relatively low value, on the order of 30–90 (e.g., 64).

The diurnal base rate, DBR, is next determined using Eq. (5) as a function of the most recently-determined second time constant, ACT_SD2(t), a specified second slope, "Slope2", and a predetermined "Sleeprate". In a similar manner, the sensor-indicated rate, SIR, may then be determined using Eq. (6) as a function of a specified first slope, "Slope1", the most recently-determined first time constant, ACT_SD1(t), and the diurnal base rate, DBR, determined using Eq. (5). The sensor-indicated rate thus determined may then be used when the pacemaker operates in a rate-responsive pacing.

From the above, it is thus seen that the diurnal base rate (DBR) is defined by Eq. (5). For a rate-responsive pacing mode, the sensor-indicated rate (SIR) may also be defined (see Eq. (6)) as a function of the diurnal base rate, i.e., the diurnal base rate serves as a "floor" for the sensor-indicated rate. By way of example, representative values used in the above expressions at a particular time of day have been determined as follows:

delay1=1 cardiac cycle, with k=128 delay2=26 seconds, with j=64

Slope1=0.6 bpm/activity unit

Slope2=2.5 bpm/activity unit

ACT_SD1(t)=+1.6 minutes (approximately)

ACT_SD2(t)=+38 minutes

Sleeprate=54 ppm.

The slope values, Slope1 and Slope2, are measured in terms of beats per minute (BPM) per activity unit. An "activity unit" represents a measure of time, usually a convenient grid size or scale of the time axis of a rate vs. time plot. For the values presented above, the activity unit is, e.g., 0.5 hours, or 30 minutes. Note further that the polarity, or sign, of the effective time constants, ACT_SD1(t) and ACT_SD2(t), will change depending upon whether the running heart average (or activity average) is increasing or decreasing.

Once the diurnal base rate has been determined as described, then the pacing interval is set to a value that is a function of the diurnal base rate, e.g., a prescribed percent P1, such as 5–10%, less than the period corresponding to the diurnal base rate (DBR). For example, using the above values as an example, the diurnal base rate at the particular time of day when determined would be:

DBR=(2.5 bpm/30 minutes) 38 minutes+54 ppm=57.2 ppm.

Because 57.2 ppm corresponds to a period (or interval) of about 1050 ms, the present invention, in order to achieve overdrive pacing, would thus set the pacing interval to a value of, e.g., 945 ms (corresponding to a pacing rate of about 64 ppm). Each time the diurnal base rate is recalculated, based on an update of the heart rate running average, the pacing interval would likewise be updated, thereby maintaining overdrive pacing at a rate that varies with the diurnal base rate.

Figure 7A:
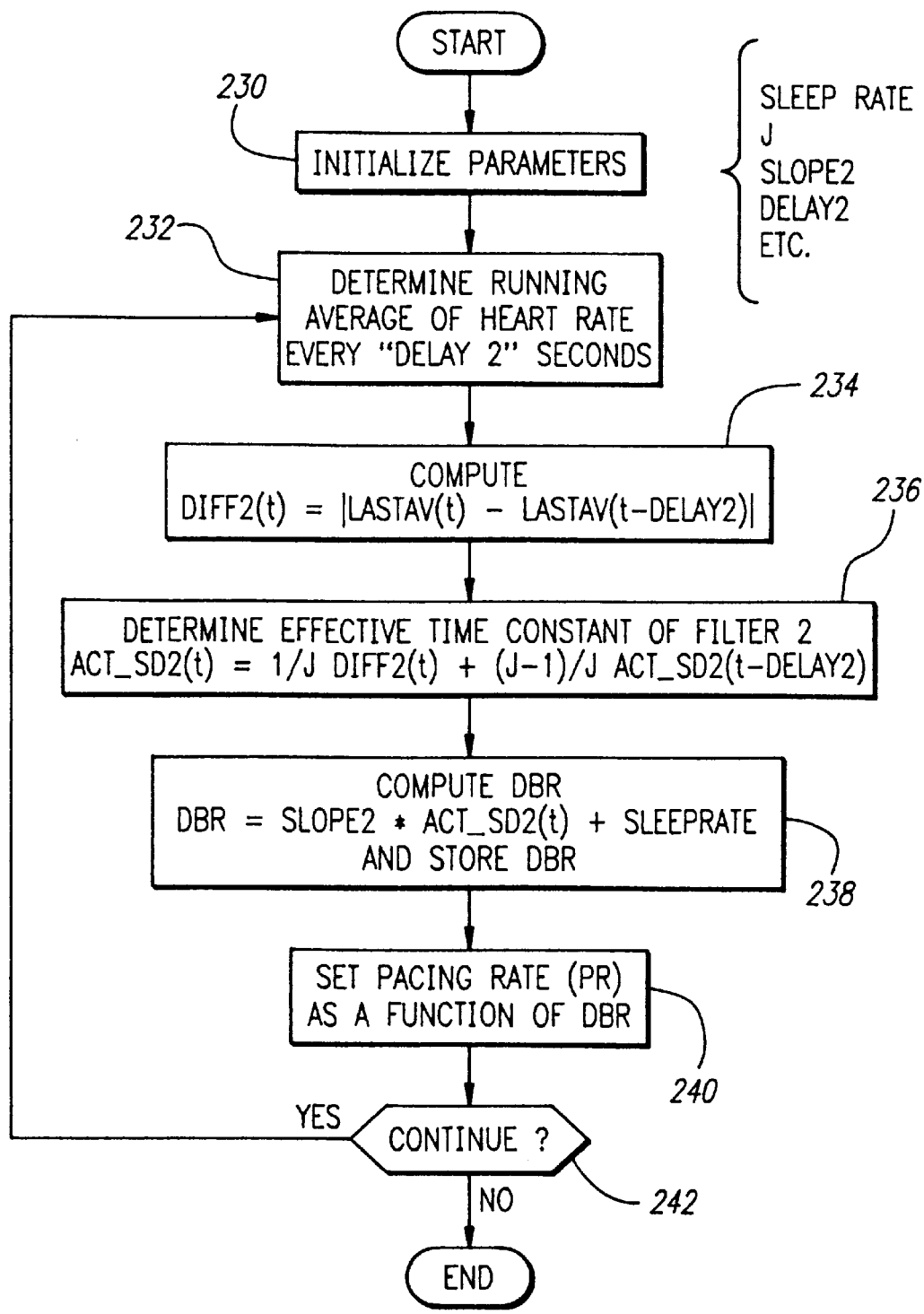
FIG. 7A shows a generalized flowchart depicting the steps employed in applying a digital, recursive filter to the heart rate/activity data using a long time constant.

The above method for determining the diurnal base rate using a recursive digital filter with a relatively slow time constant is further illustrated in a general way in the flowchart of FIG. 7A. As seen in FIG. 7A, after the relevant parameters are initialized (block 230), which parameters include, e.g., the "Sleeprate", "Slope2", "Delay2", and "J", a running average of the heart rate is determined (block 232), with such average being updated every "Delay2" seconds. In practice, such is usually accomplished by cycling through the steps of the flowchart of FIG. 7A every "Delay2" time period, sampling the sensed heart rate (or activity rate) during each pass, and using the most recent value of the sensed heart rate to update the running average. The current running average (i.e., that average determined at the present sample time "t") is denoted as "Lastav(t)"; and the prior running average (i.e., that average determined at the prior sample time "t-Delay2") is denoted as "Lastav(t-Delay2)". DIFF2(t) is then determined using Eq. (3) as the difference between Lastav(t) and Lastav(t-Delay2) (block 234). The effective time constant of the filter, ACT_SD2(t), is then computed using Eq. (4) (block 236). The diurnal base rate is then computed using Eq. (5) and saved (block 238). The pacing rate may then be set as a function of the diurnal base rate (block 240), e.g., in order to maintain overdrive pacing. If this process is to continue (YES branch of block 242), then the next pass begins (at block 232) by sampling the heart rate (or activity) after the time period "Delay2" has elapsed, and repeating the above steps. In this manner then, the diurnal base rate is regularly updated, e.g., each "Delay2" time period, and used to define an appropriate pacing rate that will achieve overdrive pacing.

Figure 7B:
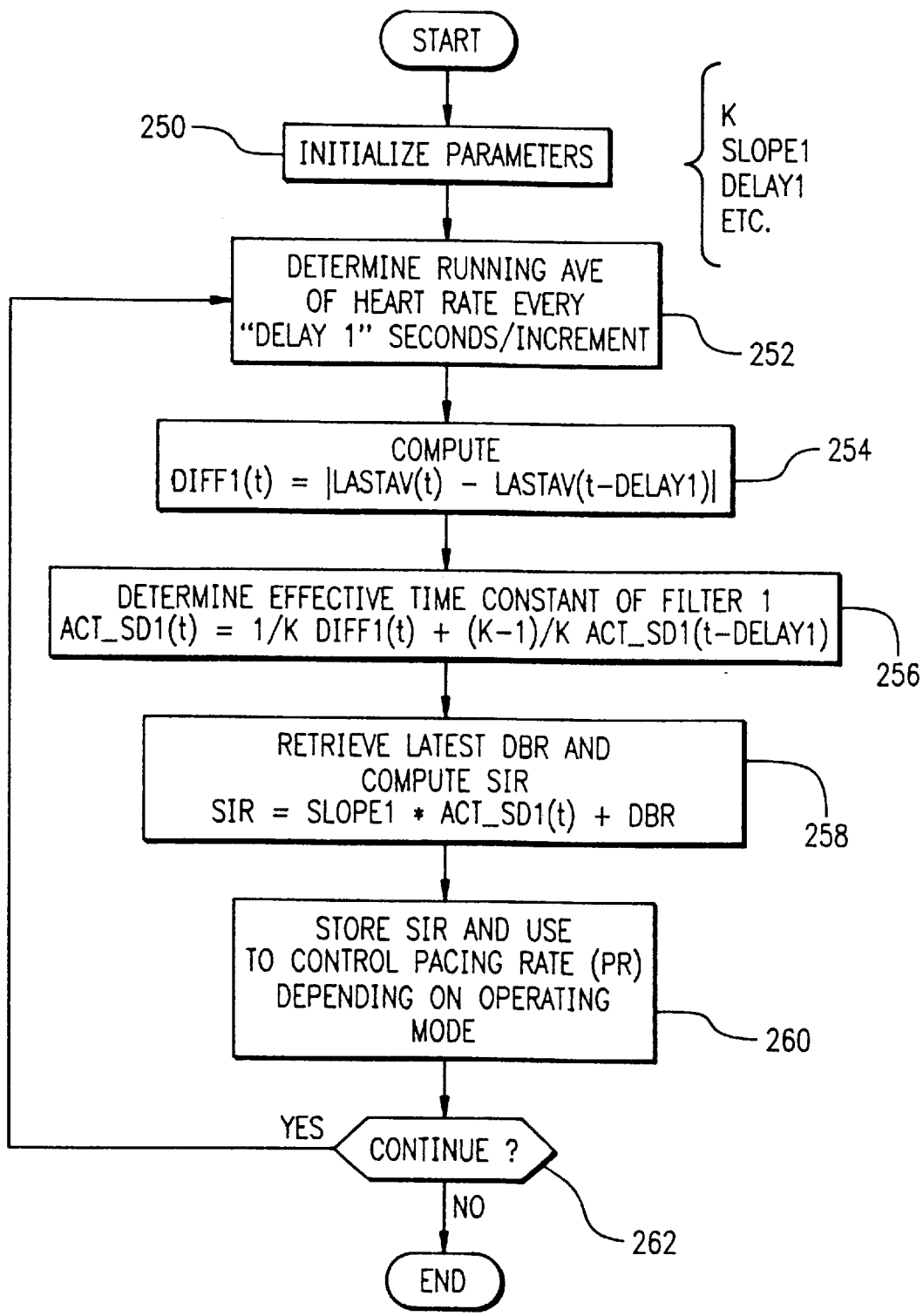
FIG. 7B shows a generalized flowchart depicting the steps employed in applying a digital, recursive filter to the heart rate/activity data using a relatively short time constant.

Similarly, the above method for determining the sensor-indicated rate using a recursive digital filter with a relatively fast time constant is illustrated in a general way in the flowchart of FIG. 7B. As seen in FIG. 7B, after the relevant parameters are initialized (block 250), a running average of the heart rate is determined (block 252), with such average being updated every "Delay1" seconds. DIFF1(t) is determined on a regular basis using Eq. (1) as a function of the most recent, Lastav(t), and prior most recent, Lastav(t-Delay1), running averages (block 254). The effective time constant of the filter, ACT_SD1(t) is then computed using Eq. (2) (block 256). The most recent value of diurnal base rate is then retrieved and used in connection with Eq. (5) to compute the sensor-indicated rate (SIR) (block 258). The value of the Sensor-indicated rate may then be stored and used, as required, to control the pacing rate of the pacemaker depending upon the operating mode of the device (block 260). This process continues (block 262) for so long as the Sensor-indicated rate is determined using recursive digital filters in the manner described.

While the flowchart of FIG. 7B is shown as a separate flowchart from that of FIG. 7A, it is noted that the two processes (one for filtering the heart rate and/or activity data with a long time constant, and the other for filtering the heart rate and/or activity data with a shorter time constant) may be combined (but do not have to be combined) in a single flowchart, and hence in a single process, with the steps of FIG. 7B, which are performed every "Delay1" time period (e.g., every n1 cardiac cycles), being nested within the steps of FIG. 7A, which are performed every "Delay2" time period (e.g., every m2 seconds).

b. Automatic Overdrive Pacing

Overdrive pacing may also be carried out based on an automatic overdrive function that automatically adjusts the pacemaker as required so that a stimulation pulse is always applied to the appropriate heart chamber, e.g., the atrium, at a rate that is faster than the patient's intrinsic rhythm. More particularly, in overdrive pacing the stimulation pulse is applied to the heart at a time in the pacing cycle which is most always prior to a natural depolarization. While different pacing schemes and approaches exist which achieve such auto overdrive function, including pacing based on diurnal rate as described above (which achieves the same function as overdrive pacing, and is thus a form of overdrive pacing), other auto overdrive functions that may be used in accordance with the invention are preferably based on either: (1) a step increase based on average atrial rate; or (2) negative hysteresis applied every cycle. These two approaches are described more fully below.

(1) Step Increase Based on Average Atrial Rate

In a dual-chamber pacemaker, the atrial rate can be monitored on either a beat-for-beat basis or for an average number of beats. Using an average number of beats to control or set the atrial rate advantageously prevents premature atrial contractions (PACs) from falsely changing the pacing rate. As a first step in applying auto overdrive pacing in accordance with this aspect of the invention, the native (or natural) average atrial rate is measured. Once measured, the pacemaker is then autoprogrammed to a base rate that is a prescribed step increment faster (in terms of rate) than the measured atrial rate. The pacing interval is then adjusted in a prescribed step increment above the new autoprogrammed base rate (i.e., faster than the base rate), on a single cycle basis, for a prescribed number of cycles. After the prescribed number of cycles (e.g., three) of stepped increases above the autoprogrammed base rate, the autoprogrammed base rate is again used to set the pacing rate.

For example, should three consecutive P-P intervals show an average rate of 60 bpm, then the base rate of the pacemaker is autoprogrammed to a programmable delta ($\Delta$) rate of 5 bpm faster than the average intrinsic rate (i.e., to 60+$\Delta$=65 bpm) to guarantee that the atria are thereafter paced faster than the intrinsic (natural) rhythm. To further assure atrial pacing, the atria are paced at increasingly faster step increments above the newly autoprogrammed base rate of, e.g, 65 bpm for a prescribed number of cycles, e.g., three cycles. For example, if the base rate is autoprogrammed to 65 bpm, as above described, then for a first cycle after such autoprogramming, the atria are paced at a rate that is the newly autoprogrammed base rate, 65 bpm, plus $\Delta$, where $\Delta$ is 5 bpm, or at a rate of 70 bpm. Then, for a second cycle, immediately following the first cycle, the atria are paced at a rate that is the newly autoprogrammed base rate, 65 bpm, plus 2$\Delta$, or at a rate of 75 bpm. Then, for a third cycle, immediately following the second cycle, the atria are paced at a rate that is the newly autoprogrammed base rate, 65 bpm, plus 3$\Delta$, or at a rate of 80 bpm. Then, for the next cycle, the pacemaker rate returns to the newly autoprogrammed base rate (or, in the case of a rate-responsive pacemaker, the sensor-indicated rate).

In the manner described above, atrial overdrive pacing is achieved, at single-cycle rates that vary in prescribed step increments over a base rate, which base rate is autoprogrammed, as required, to also assure atrial pacing. Hence, in the event that the intrinsic average atrial rate increases to a rate faster than the autoprogrammed base rate of, e.g., 65 bpm, to a newly determined average atrial rate of, e.g, 80 bpm, then the pacemaker automatically reprograms the base rate to the new intrinsic average rate plus $\Delta$, i.e., to a rate of 85 bpm.

Thus, it is seen that in accordance with this embodiment of the invention, atrial overdrive pacing is achieved by first determining an average intrinsic atrial rate and autoprogramming a base rate of the pacemaker to a value that is greater than the average intrinsic atrial rate. To further assure that atrial (overdrive) pacing is provided, the invention controls the pacemaker so that the rate of pacing automatically increases, i.e., is not the same rate cycle after cycle, above the base rate for each pacing cycle by a prescribed amount $\Delta$ of say 3–15 bpm, e.g., 5 bpm, for n consecutive cycles, where n is a programmable number of cycles of from 2–16 cycles, e.g., three cycles. After such stepped increases, the pacing rate returns to the newly autoprogrammed base rate, the sensor-indicated rate (SIR), or a minimum preprogrammed base rate, whichever is greater. Because the rate of overdrive pacing changes by an amount $\Delta$ on a cycle-by-cycle basis, the invention may sometimes be referred to as "automatic overdrive random rate pacing".

The above-described approach for achieving automatic overdrive random rate pacing is further illustrated in the flowchart of FIG. 8. As seen FIG. 8, automatic overdrive random pacing is selectively enabled (block 170), e.g., by exercising an appropriate programming command. If not enabled, then the pacing device continues to operate in its selected operating mode (block 172) in conventional manner. If automatic overdrive random rate pacing is enabled (YES branch of block 170), however, then the appropriate programming commands are made (block 173) that are used with such pacing. Such commands include, e.g., the number $m_P$ of consecutive P-to-P intervals that are measured to determine an average atrial rate, the amount of the step size $\Delta$ by which the pacing rate is increased, the number $n_P$ of consecutive cycles during which the pacing rate is increased by the step size $\Delta$, and the like.

Once enabled with the necessary operating parameters, the device performs a test (blocks 174, 176) to determine whether atrial pacing or P-wave sensing/tracking is occurring. If P-wave tracking is occurring (i.e., if P-waves are sensed), then an average atrial rate is determined (block 178) based on, e.g., the average P-to-P interval over $m_P$ consecutive cycles, where $m_P$ is a programmable integer of from (e.g., 2–32 cycles) for example, 3 cycles. Once the average atrial rate is determined, then the pacemaker rate is set for one cycle to a value that is faster than the measured average atrial rate by an amount $\Delta$ (block 180), where $\Delta$ is a programmable variable of from, e.g., 2–10 bpm, for example 5 bpm. If atrial pacing is already occurring when the P-wave tracking/atrial pacing test is performed (blocks 174, 176), then the pacemaker rate is set for one cycle to a value that is faster than the atrial pacing rate by the amount $\Delta$ (block 182). During the one cycle for which the pacing rate is increased by an amount $\Delta$ faster than the average atrial rate (as set at block 180) or faster than the atrial paced rate (as set at block 182), another determination is made as to whether atrial pacing occurs (block 184). If a P-wave is not sensed and an A-pulse is thus generated at the end of the appropriate escape interval, the pacing rate is again increased by an amount $\Delta$ (block 186), making a total of $2\Delta$ that the pacing rate has been increased from the initial atrial pacing rate or the measured average atrial rate. During such faster ($2\Delta$) one-time cycle, yet another determination is made as to whether atrial rate pacing occurs (block 188). I an A-pulse is generated due to a failure to sense a P-wave, then the pacing rate is increased again for one cycle by an amount $\Delta$ (block 190), making a $3\Delta$ total increase over the initial rate. After such faster ($3\Delta$) one-time cycle, or whenever atrial pacing does not occur (NO branch of blocks 184 and 188) the pacing rate returns to: (1) the programmed base rate, (2) the sensor indicated rate (if rate-responsive pacing is employed), or (3) the most-recently determined average atrial rate plus $\Delta$ (block 192).

Of the three possible pacing rates (two if rate-responsive pacing is not employed) to which the rate is returned at block 192, the rate selected may alternate or sequence through each rate in a prescribed pattern, i.e., return to the highest rate of the three (or two) for the first k times a return is made, return to the next highest rate for the next l times, and finally return to the lowest rate after the (l+k)th time, where k and l comprise programmable integers of from 0 to 8. Other return patterns, whether set by programming or default, may also be used. By way of example, a default return pattern may comprise always returning to the Sensor-indicated rate if rate-responsive pacing is employed, otherwise returning to the most recently-determined average rate plus $\Delta$, except every $m_P$ time returning to the base rate. Whatever rate-return scheme or pattern is employed, it is important that a new average rate be determined at regular intervals (e.g., every few minutes) so that such average rate reflects changes, both increases and decreases, in the patient's intrinsic rhythm. In this manner, overdrive pacing is achieved most cardiac cycles (which is, of course, the main goal of this aspect of preemptive tachyarrhythmia pacing), yet with the overdrive rate being somewhat different on a cycle-by-cycle basis, yet with the average overdrive rate being a rate which tracks, more or less, changes in the patient's intrinsic rhythm.

If auto overdrive pacing is to continue (YES branch of block 194), then the process repeats (blocks 174–192). If not (NO branch of block 194), then operation of the device returns to the main control branch (blocks 170, 172) so that the device can operate in a desired alternative mode of operation.

Significantly, as indicated in the flowchart of FIG. 8, when atrial pacing is detected, the pacing rate is increased by $\Delta$ only for one cardiac cycle. Within a few cardiac cycles of such one-time increase (e.g., three), the pacing rate returns back to the sensor-indicated rate, or measured average atrial rate plus $\Delta$, as explained above. In this manner, overdrive pacing is predominately achieved at rates which vary somewhat from cycle to cycle, which is a desired objective.

The pacing rate of a pacing device is typically set or adjusted by setting or adjusting the appropriate escape interval of the device. Thus, the preferred technique for achieving a faster pacing rate is to shorten the appropriate escape interval of the pacemaker, e.g., the atrial escape interval, for the cycle(s) of concern. For example, as seen in Table 1 below, a pacing rate of 60 bpm is achieved by setting the pacing interval to 1000 milliseconds (ms); whereas a pacing rate of 65 bpm is achieved by setting the pacing interval to 923.08 ms. Thus, in order to increase the pacing rate, e.g., from 60 bpm to 65 bpm, it is necessary to shorten the atrial escape interval by an amount equal to 1000−923= 77 ms so that the overall pacing interval is shortened by 77 ms. In a similar manner, a pacing rate of 70 bpm is achieved by setting the pacing interval to about 857 ms, and thus a step increase in the pacing rate from 65 bpm to 70 bpm is achieved by shortening the pacing interval (e.g., by shortening the atrial escape interval) by an amount equal to 923−857=66 ms. In like manner, other step changes in the pacing rate are achieved by adjusting the pacing interval by the amounts shown in Table 1.

TABLE 1

Pacing Intervals Used For Selected Pacing Rates

| To Change From a Pacing Rate of: | (Having a Pacing Interval of:) | To a Pacing Rate of: | (Having a Pacing Interval of:) | Change the Pacing Interval By an Amount: |
|---|---|---|---|---|
| 60 bpm | 1000 ms | 65 bpm | 923.08 ms | 76.92 ms |
| 65 bpm | 923.08 ms | 70 bpm | 857.14 ms | 65.94 ms |
| 70 bpm | 857.14 ms | 75 bpm | 800 ms | 57.14 ms |
| 75 bpm | 800 ms | 80 bpm | 750 ms | 50.00 ms |
| 80 bpm | 750 ms | 85 bpm | 705.88 ms | 44.22 ms |
| 85 bpm | 705.88 ms | 90 bpm | 666.67 ms | 39.21 ms |

It should be pointed out, that while the above description of the invention refers to a step change in the pacing rate of Δ bpm, where Δ is a fixed number, e.g., 5 bpm, the invention is not limited to a fixed step change in the pacing rate. For example, different values of Δ may be used. To illustrate, if the base rate is f0, then one variation of the invention is to set the pacing rate of a first cycle after detecting atrial pacing to f1=f0+Δ1, a second cycle to f2=f1+Δ2, a third cycle to f3=f2+Δ3, and so on, with a different step size in pacing rate Δi being used each time an adjustment is made to the pacing rate.

Additionally, as the above description of the invention makes clear, the invention is not limited to having a user select step changes in the pacing rate, but also applies to selecting changes (whether fixed or variable) in the pacing interval. That is, rather than requiring a user to select Δ to be, e.g., 5 bpm; the user may instead select a change in the pacing interval of δ ms, where δ is a fixed or variable time interval of, e.g., 50 ms. What is important for the invention is that when enabled some change (preferably a dynamic change) be made temporarily in the pacing interval (or the pacing rate) in order to assure that overdrive pacing be realized during most cardiac cycles.

A simplified electrogram (EGM) timing diagram that illustrates the above-described auto overdrive pacing technique is shown in FIG. 9A. The EGM timing diagram of FIG. 9A comprises a simplified representation of the main events which occur (e.g., P-waves, A-pulses, and R-waves), as well as the main atrial escape interval (AEI) used during a sequence of cardiac cycles. The AEI is depicted in FIG. 9A as a horizontal time line (which represents the passage of time along the horizontal axis), with an arrow head being shown on the right end of the time line when the AEI times out without a P-wave having been sensed (in which case an A-pulse is delivered and atrial pacing occurs), and with a "dot" being shown on the right end of the line when a P-wave is sensed before the AEI times out (in which case no A-pulse is delivered, and P-wave tracking occurs). For simplicity, an R-wave is shown in FIG. 9A to represent a ventricular event (i.e., a ventricular depolarization and/or contraction), regardless of whether such ventricular event is a natural or paced event.

In FIG. 9A, it is assumed that the base rate of the pacemaker has been set to a rate f0 corresponding to a pacing interval of T0. It is also assumed that the number of consecutive cardiac cycles during which a step change in the pacing rate occurs has been set to three. (These parameters are, of course, programmable, and could be set to any value suited to meet the needs of a given patient.) As seen in FIG. 9A, a first P-wave P1 is sensed, followed by a second P-wave P2, a third P-wave P3, and a fourth P-wave P4, indicating P-wave sensing is occurring. An average P-to-P interval, $T_{AVE}$, may thus be determined as the average of the time interval between P1 and P2 (1st P-to-P interval), the time interval between P2 and P3 (2nd P-to-P interval), and the time interval between P3 and P4 (3rd P-P interval). In accordance with the present invention, once the average P-to-P interval, $T_{AVG}$, has been determined, the atrial escape interval, $AEI_1$, is then set to a new value, T1, where T1 is less than $T_{AVG}$. (T1, for example, may be equal to the pacing interval corresponding to a pacing rate that is 5 bpm faster than the base rate f0.) As illustrated in FIG. 9A, in the next cardiac cycle following the shortening of AEI to $AEI_1$, the AEI times out without a P-wave having been sensed, causing an atrial stimulation pulse, A1, to be generated. In accordance with the preemptive tachyarrhythmia pacing scheme of the present invention, the AEI of the next cardiac cycle following the A-pulse A1, $AEI_2$, is shortened for one cycle to a value T2. No P-waves occur during the timing out of $AEI_2$, hence an A-pulse A2 is generated when $AEI_2$ times out. The AEI for the next cardiac cycle following the A-pulse A2, $AEI_3$, is further shortened for one cycle to a value T3. No P-wave occurs during the timing out of $AEI_3$, causing an A-pulse A4 to be generated as soon as $AEI_3$ times out. The timing out of $AEI_3$ represents the end of the third cycle during which a shortened pacing interval (faster pacing rate) has been invoked. Hence, the value of AEI for the next cycle returns to $AEI_1$, corresponding to a pacing interval of T1. The next three consecutive cycles use different values of AEI, e.g., $AEI_1$, $AEI_2$, $AEI_3$, and the process repeats. Eventually, following an A-pulse $A_j$, where j is an integer, and in accordance with a prescribed pattern, the value of AEI returns to its base value T0. For example, AEI may return to T0 after 64–256 overdrive pacing cycles have occurred, or after a prescribed period of time (e.g., 1–5 minutes) of overdrive pacing has elapsed. With the value of AEI extended to its base value, a P-wave $P_{j+1}$ is sensed. Other P-waves (not shown) may then also be sensed, allowing a new average P-wave rate (or atrial rate) to be measured, from which an updated value of $T_{AVG}$, and an updated value of $AEI_1$, may be determined. The process then repeats, thereby providing atrial overdrive pacing at a variable pacing rate.

It is contemplated by the inventors that the particular manner of realizing a variable-rate atrial overdrive pacing as described above in FIG. 9A is not the only way to achieve variable-rate atrial overdrive pacing. For example, instead of gradually increasing the pacing rate over $n_P$ cardiac cycles, and then dropping back to the initial paced rate, and repeating this sequence over and over, as shown in FIG. 9A, it would also be possible to initially make a larger step increase in the pacing rate and then gradually decreasing the pacing rate over $n_P$ cardiac cycles. That is, whereas FIG. 9A illustrates an atrial overdrive pacing sequence that comprises, e.g., 70, 75, 80, 70, 75, 80, . . . ppm, a similar (and perhaps equally suitable, for most patients) atrial overdrive sequence could be, e.g., 80, 75, 70, 80, 75, 70, . . . ppm. Likewise, other atrial overdrive pacing sequences could be used, e.g., 70, 73, 76, 80, 76, 73, 70, 73, 76, 80, 76, 73, 70, . . . ppm; or 70, 70, 72, 72, 74, 74, 76, 76, 78, 78, 80, 80, 70, 70, 72, 72, . . . bpm. Indeed, the invention contemplates a wide variety of different pacing sequences. Any sequence which maintains overdrive pacing with a pacing rate that varies in a prescribed manner could be used.

Turning next to FIG. 9B, a representation of a canine EKG waveform is depicted which illustrates the actual operation of auto atrial overdrive pacing using the basic techniques described above. FIG. 9C depicts a rate verses time graph, with rate samples being taken every event (i.e., every cardiac cycle), corresponding to the canine EKG of FIG. 9B. As the rate verses time graph of FIG. 9C illustrates, the heart cycles or varies about a mean of approximately 95 bpm. As further seen on the left side of FIG. 9B, P-waves, $P_1$–$P_5$, and R-waves, $R_1$–$R_5$, occur in a normal sequence, suggesting a stable, non-paced cardiac rhythm. That is, P-wave $P_1$ is followed by R-wave $R_1$ during a first cardiac cycle. Similarly, P-wave $P_2$ is followed by R-wave $R_2$ during a second cardiac cycle. Thus, an average P-P wave interval, $T_{AVG}$, can be readily determined as the time interval between consecutive P-waves, e.g., between P-wave $P_4$ and $P_5$.

In order for normal P-wave sensing to occur, as shown on the left side of FIG. 9B, it is thus necessary that the atrial escape interval (AEI) of the pacemaker be set to some value T0 which is greater than $T_{AVG}$. However, as soon as an atrial overdrive pacing mode is enabled (e.g., following P-wave $P_9$), the AEI of the pacemaker is shortened to a value T4, where T4 is less than $T_{AVG}$ by a large step size. With such a shortened AEI, an A-pulse $A_1$ is thus generated as soon as T4 times out. The AEI of the next cycle is increased by a small step size to T5, where $T_{AVE}$<T5<T4. Hence, when T5 times out, another A-pulse $A_2$ is generated. The AEI of the next cycle is again increased by a small step size to T6, where $T_{AVE}$<T6<T5<T4. Thus, upon the timing out of T6, yet another A-pulse $A_3$ is generated. For the particular situation shown in FIG. 9B, the AEI of the cycle following the A-pulse $A_3$ is again increased, e.g., to a value that is greater than $T_{AVE}$. Hence, a P-wave $P_{10}$ occurs before the increased AEI times out. The occurrence of such P-wave $P_{10}$ triggers a repeat of the shortened AEI cycles. That is, the AEI of the cycle following the P-wave is shortened to T4, causing an A-pulse $A_4$ to be generated at the expiration of T4, and with the AEI of the next cycle being increased slightly to T5, following which another A-pulse $A_6$ occurs, and so on. The atrial overdrive paced rate for the canine experiment shown in FIG. 9B may thus be represented as a sequence of, e.g., 105, 100, 95, 90 (non-paced), 105, 100, 95, 90 (non-paced) . . . bpm.

In accordance with a variation of the invention, note that the amplitude of the A-pulses A, A- and A, shown in FIG. 8 may decrease as the length of the AEI increases. This variation helps assure that capture always occurs at the shorter escape intervals.

(2) Negative Hysteresis Applied Every Cycle

Yet another way to achieve automatic atrial overdrive pacing, and hence provide a preemptive tachyarrhythmia pacing scheme, in accordance with the present invention is to apply negative hysteresis every cardiac cycle. Normal (or positive) hysteresis is commonly employed in modern programmable pacemakers in order to allow patients to benefit from their own intrinsic rhythm as often as possible. Such hysteresis is typically used relative to the ventricular channel of the pacemaker. Thus, for example, where positive hysteresis is employed, for so long as an R-wave is sensed (evidencing a natural ventricular contraction), the appropriate interval (e.g., the AV interval of the pacemaker) is lengthened. However, if pacing must occur, then the interval is shortened. The appropriate interval thus toggles between a short (or normal) value whenever pacing occurs, and a longer (or hysteresis) value whenever sensing occurs.

Negative hysteresis, like positive hysteresis, also employs two escape interval values. However, when using negative hysteresis the shorter value of the two escape interval values is invoked to encourage pacing, rather than discourage it.

The present invention, in accordance with one embodiment thereof, utilizes negative hysteresis in connection with the atrial channel of the pacemaker in order to maintain atrial pacing. A programmable hysteresis interval (e.g., termed the negative hysteresis delta) is selected to assure that atrial overdrive pacing is maintained. The atrial pacing interval is maintained at the programmed base rate or the sensor-indicated rate. Whenever an intrinsic P-wave is detected within the atrial escape interval, the atrial escape interval (AEI) is automatically shortened by the negative hysteresis delta, so that the next cycle is subjected to such shortened AEI. The shortened AEI is maintained for a prescribed period of time, or for a prescribed number of cardiac cycles, at which time the AEI is returned to its normal value, either in one step, or gradually over several cycles.

Thus, it is seen that negative hysteresis provides a type of beat-to-beat monitoring which dynamically adjusts the AEI to maintain atrial pacing. For example, if atrial pacing is being provided at 70 bpm, and if a premature atrial contraction (PAC) occurs which changes the effective rate to 74 bpm, then the negative hysteresis feature automatically steps in to increase the atrial paced rate (shorten the atrial escape interval) by, e.g., 5%. Such increased atrial rate is maintained for a prescribed number of cardiac cycles (e.g., 32–256) or for a prescribed period of time (e.g., 1–5 minutes), at which time the paced rate may be gradually decreased to a prescribed rate (e.g., to a value that is 5–100 lower than the current paced rate), or gradually decreased until an intrinsic P-wave is sensed.

Advantageously, using negative hysteresis in the manner described herein to maintain atrial overdrive pacing may increase the effective atrial-to-ventricular (AV) conduction time and permits titrating the AV interval of the pacemaker to a potentially longer value, but still provides a hemodynamically improved paced AV delay, particularly relative to that achieved in a conventional PV atrial synchronous—ventricular pacing mode. Further, atrial overdrive pacing prevents the spontaneous generation of atrial arrhythmias because of the regulating nature of negative hysteresis.

Pacing with Randomicity

Referring momentarily back to FIG. 3, it is seen that another type of preemptive tachyarrhythmia pacing (PTP) that may be employed in accordance with present invention is pacing with randomicity. Pacing with randomicity, as suggested in FIG. 3 may be invoked either: (1) by itself to maintain a specified degree of chaos in the pacing interval, without regard to whether overdrive pacing is achieved; or (2) as a means for maintaining overdrive pacing exhibiting a degree of randomness. More particularly, in accordance with this embodiment of the invention, pacing with randomicity refers to a system and method for adjusting the rate of stimulation using chaos theory for the purpose of preventing lethal arrhythmias.

As is known in the art, chaos is a nonlinear, predictable order without periodic repetition. From a mathematical standpoint, chaos is defined as "a complicated, aperiodic, attracting of orbits of certain dynamical systems". While chaotic systems may appear random, "they are in fact determined by very simple mathematical formulas . . . which are extremely sensitive to initial conditions." See, e.g., "Chaos, Other Nonlinear Dynamics Research May Have Answers, Application for Clinical Medicine", *The Journal of the American Medical Association* (JAVA), Vol. 266, No. 1, pp. 12–18 (Jul. 3, 1991).

Several attempts have been made to utilize chaos stabilizing algorithms to convert arrhythmia activity of the heart to stabilized periodic behavior. See, e.g., U.S. Pat. Nos. 5,342,401; 5,447,520; and 5,456,690; as well as Smith et al. "Electrical Alternans and Cardiac Electrical Instability," *Circulation*, Vol. 77, No. 1, pp. 110–121 (January 1988). Of particular interest here is the approach taken in U.S. Pat. No.

5,447,520, issued to Spano et al., and U.S. Pat. No. 5,201,321, issued to Fulton. Both the Spano et al. and Fulton patents are incorporated herein by reference.

Spano et al. teaches a procedure for stabilizing an erratic heart beat by recognizing that the chaotic regime of cardiac tissue is characterized by natural motion of interbeat interval points along unstable paths toward or away from an unstable fixed point, and that such chaos is controllable by a properly delayed intervention of injected electrical stimuli tending to shorten the interbeat interval.

Fulton teaches diagnosing the vulnerability of a patient's heart to lethal arrhythmias according to chaos techniques to obtain an indication of heart condition. For example, Fulton computes and monitors a variable termed the "correlation dimension ($D_2$)". Should the correlation dimension $D_2$ ever decrease from a value of about 2.0 or greater to a value of about 1.0, that indicates an alarm condition because the patient is deemed to be at great risk for a lethal arrhythmia.

In accordance with the presently-discussed pacing-with-randomicity embodiment of the invention, a pacing system or method is provided wherein the correlation dimension $D_2$ is monitored (as in Fulton, see, e.g., col. 11, line 20, through col. 13, line 12) and the stimulation rate (i.e., the pacing/stimulating interval of the device, whether a pacemaker or a defibrillator) is varied on a beat-by-beat basis in an attempt to maintain $D_2$ at a value that is equal to 2.0 or more. By maintaining a variation in the pacing/stimulating interval on a beat-by-beat basis in this manner, the correlation dimension is not allowed to decrease to 1.0, and the patient thereby avoids the risk of a lethal arrhythmia, at least insofar as a lethal arrhythmia can be predicted by a decrease in the correlation dimension from a value of 2.0 or higher to a value of about 1.0, as taught by Fulton.

The variable pacing/stimulating interval may be set solely based on the requirements needed to maintain the correlation dimension at or above 2.0; or it may be set to always provide a pacing/stimulating rate that is greater than an estimated natural pacing rate (e.g., an average atrial rate), thereby assuring a correlation dimension greater than 2.0 in combination with overdrive pacing.

The basic technique for varying the pacing/stimulating rate in accordance with this embodiment of the invention is shown in the flowchart of FIG. 10. As seen in FIG. 10, once the appropriate pacing with randomicity variables have been initialized (block 220), the correlation dimension $D_2$ is determined by monitoring the appropriate pacing parameters (e.g., the most recent pacing intervals or, using the terminology of Fulton, the "beat timing vectors"), which are compared with previously monitored and stored pacing interval values. A determination is then made as to whether $D_2$ is greater than or equal to 2.0 (block 224). If it is (YES branch of block 224), then monitoring of the pacing intervals to determine $D_2$ continues (block 222). If it is not (NO branch of block 224), then the pacing interval is adjusted as required in an attempt to steer $D_2$ to a value that is greater than or equal to 2.0 (block 226). So long as pacing with randomicity is to continue (YES branch of block 228), then the above process continues (blocks 222, 224, 226), adjusting the pacing parameters, e.g., pacing interval, as required in order to keep $D_2 \geq 2.0$ If a command is received to cease pacing with randomicity, as might occur, e.g., when the device is reprogrammed or reconfigured, then further adjustment of the pacing parameters to maintain $D_2$ at or above 2.0 ceases (NO branch of block 228).

As is evident from the manner in which the correlation dimension $D_2$ is determined (see, e.g., FIGS. 16A–16G of Fulton and accompanying text), $D_2$ is a cumulative measure of the change in the pacing interval (or beat timing vector) compared with a previously stored value of the pacing interval (or beat timing vector). Thus, the adjustment of the pacing interval (at block 226 of FIG. 10) to steer $D_2$ in a direction that will cause it to assume a value greater than or equal to 2.0, will typically be made by either shortening or lengthening the next pacing interval. In practice, such adjustment of the pacing interval may be guided by selecting a suitable adjustment scheme or pattern (block 227), e.g., as part of the initialization (block 220). Such scheme or pattern, for example, may automatically toggle between shortening the pacing interval during one cycle, and lengthening the pacing interval during the next cycle, with such shortening/lengthening being done to move $D_2$ in a direction that causes it to be $\geq 2.0$. Shortening or lengthening, or other desired scheme or pattern, could also randomly selected, e.g., using a random selection algorithm. Alternatively, a selection algorithm may be utilized which shortens or lengthens the current pacing interval as a function of whichever (shortening or lengthening) produces a pacing interval closest to (or farthest from) a preselected maximum or minimum pacing interval. Indeed, there are numerous different ways contemplated by which the current pacing interval may be adjusted in order to move or maintain the correlation dimension $D_2$ in a direction that is at or above a value of 2.0, any of which would be suitable for purposes of the present invention.

Further, it is contemplated that the threshold value of the correlation dimension $D_2$ that is maintained by adjusting the pacing interval may be a programmable parameter, selected by the physician or cardiologist (or other medical personnel) at the time of implantation or thereafter. That is, for some patients, it may be desirable to maintain the value of $D_2$ at 1.8 or 1.9, instead or 2.0. For still other patients, it may be determined that $D_2$ should be maintained at 2.1 or 2.2, instead of 2.0. The present invention advantageously allows flexibility in this regard.

Pacing Based on Sensed Parameters

A further technique that may be used in accordance with the present invention to provide preemptive tachyarrhythmia pacing (PTP) is pacing based on sensed parameters. By "sensed parameters", it is meant any parameter sensed by appropriate sensing circuits contained within, or coupled to, the implantable medical device (e.g., the implantable pacemaker, or defibrillator). Sensed parameters include, for example, physiological parameters such as blood pressure, contractility, pre-ejection interval, intrachamber impedance, stroke volume, $O_2$ saturation, and the like. Sensed parameters may also include the sensed heart rate, e.g., the presently-sensed atrial rate, especially when compared with a prior atrial rate. Sensed parameters may further include the presently sensed morphology of the intracardiac electrogram (IEGM) signal, particularly when compared against a prior template of the IEGM signal.

In accordance with this aspect of the invention, the pacemaker and/or defibrillator device, in addition to being equipped with an appropriate sensor(s) and related circuitry, is fitted with enhanced memory capacity which allows the device to serve as a monitor of the cardiac cycle. As such, the device is able to "learn" over time that which is normal for the patient within whom the device is implanted. Then, based upon specific spontaneous behavior that varies from the "usual" or "normal", a trigger signal is generated that modifies the behavior of the device with the intent of preventing a tachyarrhythmia. In a broad sense, this approach is that which is shown in the generalized flowchart of FIG. 4. That is, as shown in FIG. 4, when operating in a preemptive tachyarrhythmia pacing (PTP) mode, a desired preemptive tachyarrhythmia pacing algorithm is selected (block 132), the needed sensors are enabled (block 134), and base-line data is gathered or otherwise acquired (block 136) in order to define what is "normal" or in order to allow the device to "learn" what is "normal". A threshold is also set or otherwise defined which specifies just how far from "normal" the performance of the device may deviate before the desired preemptive tachyarrhythmia pacing algorithm is invoked (block 138). Then, the performance of the device is monitored (block 142), e.g., by monitoring the output of the enabled sensor(s), to determine if such operation is "normal". When a determination is made that the operation is not normal (YES branch of block 144), then the selected Preemptive tachyarrhythmia pacing algorithm is invoked (block 146), which invoked algorithm is designed to prevent a tachyarrhythmia from occurring.

The invention thus takes advantage of increased memory and data processing capabilities of the pacemaker or defibrillator device to recognize changes in the underlying rhythm, or other factors (detected by one or more sensors), associated with the development of a tachyarrhythmia. Recognition of the arrhythmia substrate in this manner advantageously allows the system to modify its behavior only at that time when the risk of a tachyarrhythmia is increased. Such modification of the device behavior not only avoids the occurrence of susceptible tachyarrhythmias, but also minimizes or eliminates the need for sustained periods of pacing at relatively rapid rates when such is not required. Further, it is anticipated that preemptive tachyarrhythmia pacing, as described herein, also eliminates the need for extensive surgical procedures, and may even allow the discontinuance of medications, thereby avoiding the potentially adverse side effects of pharmacologic therapy.

PTP Example

By way of a specific example, consider the classical pathologic tachyarrhythmia, including its common causes, as discussed below in Appendix A. With enhanced memory capacity, the pacemaker serves as a monitor of the cardiac cycle. As such, it is able to "learn" the mean rate associated with a stable atrial or ventricular rhythm. An example of a preemptive tachyarrhythmia pacing (PTP) algorithm that may be used in such instance may be patterned as follows: Changes in the rhythm that occur slowly (where "slowly" is a relative term defined as a percentage, e.g., <10–15%, of the average cycle length) may be ignored because such changes are likely natural changes associated with varying physical activity (e.g., exercise or rest). Abrupt changes as would be expected to occur with a single premature beat (where "premature" is again defined as a percentage, e.g., 40–60%, of the mean or average cycle length) may be treated and labeled as a premature beat. Then, rather than allow a return of pacing at the previous cycle length (as would occur if waiting for the next P-wave for the AAI or DDD modes or R-wave in the DDI or VVI modes, with or without rate modulation), the invention preempts the usual rate controls in order to increase the basic pacing rate to a rate which is faster than the mean rate, but slower than the single beat rate determined by the premature beat. This action prevents the pause that would otherwise normally follow a premature complex, thereby reducing the likelihood of recurrent premature beats (bigeminy); and further reduces the temporal dispersion of refractoriness, and thereby minimizes or prevents subsequent premature beats from initiating a tachycardia.

Once a faster rate is initiated in this manner, there must also be some means of returning the system to its programmed base rate, sensor-indicated rate or P-wave defined rate (for the purposes of this discussion, all these rates will be termed the "base rate"). Hence, in accordance with this example of a preemptive tachyarrhythmia pacing algorithm, the faster rate is maintained for either a programmable period of time or a programmable number of cycles before the rate begins to return to the base rate. The effective paced rate (AAI, DDI or VVI) may be progressively slowed based upon a percentage of the pacing cycle length, or in accord with the programmed Recovery Time if rate modulation is enabled. If rate modulation is not enabled, the return should be based upon the Slow or a Very Slow recovery time as a default setting, or be based on a programmable variable.

Should recurrent premature beats occur as the rate slows, the rate promptly returns to the higher rate.

In the manner described above, then, the rate is allowed to increase to a higher rate and/or decrease back to the base rate as controlled by the Preemptive tachyarrhythmia pacing algorithm.

Several programmable options exist when using such preemptive tachyarrhythmia pacing algorithm, including:

(1) Cycle length change that will be treated as a premature beat. Anything greater than the specified change is considered as a normal rate fluctuation. To allow for changing physiologic substrates any change should be based upon a percentage of the mean cycle length (a phenomenon termed adaptive), but the patent should also allow for a programmable fixed millisecond coupling interval.

(2) Duration of pacing at the more rapid rate. This programmed option is set as either a programmable period of time (e.g., 15, 30, 60 seconds; 2, 3.5, 5, 10 minutes) or a programmable number of cycles (e.g., 10 to 1000). Both of these options may be based upon the clock cycle within the pacemaker.

(3) Return to baseline. The Return-to-Baseline option is based upon the Recovery time options in the rate-modulated mode. If rate-modulation is enabled, the programmed recovery time becomes the default setting, unless another setting is specifically made which overrides the default setting without affecting the Recovery Time during normal rate-modulation. If rate-modulation is not enabled, then the default setting is either Slow or Very Slow—basically the slowest option allowed by the system (although, here too, an override option is made available to the physician).

(4) Functional Mode during preemptive pacing. This is a mode-switching type of algorithm where the mode of the device is switched to a functional mode whenever preemptive pacing is to occur as a function of, e.g., mode-mapping selections that may be set when the device is programmed.

If the programmed mode is a single chamber mode, the system continues to function in that mode at the faster rate.

If the programmed mode is DDD, the functional mode is DDI since the atrial paced rate will be faster than the endogenous atrial rate. The functional mode should not be DVI because atrial competition could occur in the presence of another atrial premature beat.

If the programmed mode is DDI, the preemptive mode will also be DDI. If rate modulation is enabled in any of these modes, the functional mode is not rate modulated until the rate has returned to the sensor-indicated rate since, by definition, the premature beat occurs at a rate which is faster than that defined by the sensor. As such, the preemptive increase in rate should exceed the sensor-indicated rate.

If the programmed mode is VDD, the preemptive mode should be VVI. To allow the algorithm to be applied to all products, if the highest allowed mode is VDD, the functional mode should be VVI, which could be the case in a single lead VDD system.

If the highest functional mode is DDD, but the unit is programmed to VDD, the unit will function as in the DDI mode with autoprogramming to a high atrial output to maximize the chance of atrial capture. It is also possible to program to the VDD mode in the presence of high atrial capture thresholds if the patient has high grade AV block, and only rarely or never needs AV pacing at the programmed base rate, thus forgoing atrial pacing in an effort to reduce battery current drain or avoid extracardiac muscle stimulation (such as the diaphragm via the phrenic nerve or direct stimulation of the pectoral muscle). An option may also be provided to disable the Preemptive tachyarrhythmia pacing algorithm when pacing in the VDD mode.

(5) Triggering event—The triggering event would be the atrial premature beat or ventricular premature beat. Depending upon the patient's clinical problem, the specific premature event that initiates this example of the Preemptive tachyarrhythmia pacing algorithm should be programmable (unless the pacemaker is programmed to the single chamber mode). The following triggering events may be used:

AAI mode—trigger event is a premature atrial sensed event.

VVI mode—trigger event is a premature ventricular sensed event.

DDI or DDD mode—trigger event is programmable to be either an atrial or ventricular sensed event. If the patient has known supraventricular tachycardias, an atrial premature event should generally be chosen. If the patient has ventricular tachycardia or ventricular fibrillation, then a premature ventricular sensed event should generally be chosen.

VDD mode in single lead VDD system—trigger event should generally be a ventricular premature event, unless the capability of high output via the atrial channel is to be added for this algorithm, in which case an atrial premature beat could also be selected as the trigger event.

VDD mode in the dual lead DDD system—trigger event could be either an atrial or ventricular premature beat in the VDD mode where the pacemaker is capable of DDD function. If an atrial sensed event is chosen, then the system should go to DDI with a high atrial output while the Preemptive tachyarrhythmia pacing algorithm is active.

The preemptive tachyarrhythmia pacing algorithm described in the present example may advantageously be included in selected tachyarrhythmia products as a means minimizing the need for either antitachycardia pacing [ATP] or delivery of a shock. The preemptive tachyarrhythmia pacing algorithm may also be included in bradycardia products. Unlike pure antitachycardia pacing products, however, the preemptive tachyarrhythmia pacing algorithm offers an even lower chance of inducing a tachycardia because neither the atrium nor ventricle are stimulated at a rate which is faster than that defined by the coupling interval between the basic complex and a premature beat. Thus, in theory, the preemptive tachyarrhythmia pacing algorithm may be incorporated in a pure bradycardia product, and does not require back-up defibrillation capability. Further, at least on the atrial channel, the preemptive tachyarrhythmia pacing algorithm described in the example may be another means of reducing the incidence of atrial fibrillation and/or the need for a pure atrial defibrillator.

It is to be emphasized that the present invention is not limited by the specific preemptive tachyarrhythmia pacing algorithm example, and its variations, set forth above. The preemptive tachyarrhythmia pacing algorithm, in its most general form, requires sufficient memory in the device so that it can "learn" what is normal for that patient; and then, based upon specific spontaneous behavior that varies from the "usual" or "normal", modify the behavior of the device with the intent of preventing a tachyarrhythmia. The specific preemptive tachyarrhythmia pacing algorithm example set forth above focuses on the prevention of bradycardia-dependent arrhythmias. Specifically, the premature beat (early cycle) is followed by a longer cycle due to either resetting the sinus mechanism or blocking conduction of the atrial depolarization to the ventricle. This longer cycle or pause is actually one cycle of an absolute or relative bradycardia and the Preemptive tachyarrhythmia pacing algorithm, as described, is intended to prevent this relative bradycardia, and thereby hopefully prevent any tachyarrhythmias that may result from the cascade of events that frequently follow the longer cycles or slower rates.

As previously indicated, however, the present invention may include any electrical or sensor-based parameter, or combination of parameters, that the implanted device can learn, and then modify the pacing system behavior in response to any deviations from the normal that have been associated with development of a tachyarrhythmia. The "template" that is learned to define the normal may be either: (1) a "one shot" operation wherein the normal template is learned and then retained, or (2) a continuously updated template. In either case, only marked abrupt changes from the "normal template" trigger a specific change in the device behavior. Thus, while the algorithm is properly referred to as a "preemptive tachyarrhythmia pacing" algorithm, it should also be recognized that the preemptive tachyarrhythmia pacing algorithm may additionally modify the response to a tachyarrhythmia depending upon the particular parameter which is being monitored.

Examples of some parameters that may serve as an appropriate trigger for use with the invention, in addition to those already mentioned above (e.g., blood pressure, contractility, pre-ejection interval, intrachamber impedance, stroke volume, $O_2$ saturation, etc.) include:

A. Heart Rate Variability (HRV). Normal patients tend to have a marked fluctuation in heart rate variability even over a period of a few minutes. In contrast, patients with severe cardiac dysfunction who are prone to an increased incidence of ventricular tachyarrhythmias have a marked reduction in HRV. Unfortunately, individuals with other diseases such as poorly controlled diabetes mellitus or autonomic dysfunction also have a reduction in HRV. Still, pacemakers are implanted in patients who have heart disease rather than diabetes or the other problems, although they may have these as concomitant conditions.

In addition, the algorithm may monitor the intrinsic atrial rhythm for HRV, since the two primary indications for pacing are AV block or sinus node dysfunction. Sinus Node Dysfunction patients would not be a candidate for this parameter.

When HRV is incorporated in a defibrillator, only those patients who have a primary need for bradycardia pacing support (typically a minority of patients) are generally candidates for an algorithm which utilizes HRV.

B. Ischemia. High frequency signals within the QRS complex may be used for the identification of ischemia.

Such high frequency signals may thus be termed as "Cardiac Activity Signals". Studies completed to date relative to such cardiac activity signals have used only surface ECG leads, but the results appear somewhat promising. It is yet to be determined whether the results will be the same from a single endocardial lead looking at the right ventricular electrogram where a pacing lead is typically located, although left ventricular endocardial electrograms have provided information during percutaneous transluminal coronary angioplasty (PTCA) induced ischemia. Ischemia, however, is often a substrate for the development of tachyarrhythmias. Ischemia may also be induced by too rapid a heart rate or an inappropriate AV delay. Thus, a marker for ischemia, such as the high frequency cardiac activity signals herein described, when identified, may be used in accordance with the invention to trigger a change in the pacemaker's behavior to either modify the AV delay or slow the heart rate (assuming atrial or AV pacing) in an effort to reduce ischemia and hence, prevent arrhythmias as well as some of the other dire consequences of myocardial ischemia, such as a myocardial infarction (heart attack).

C. Late Potentials. Signal averaged electrocardiograms (SAECGs) have identified "late potentials" from the surface ECG leads, often using the X, Y, and Z leads to examine the cardiac electrical activity in three different planes. These have correlated very effectively with an increased risk of ventricular tachyarrhythmias. It has been shown that late potentials in P-waves (signal averaged atrial electrocardiograms) may correlate with an increased incidence of atrial tachyarrhythmias. No one, to Applicants' knowledge, has shown a similar correlation with an endocardial electrogram, particularly one fixed at a single site. At the present time, late potentials are "fixed" in that they do not fluctuate with a changing substrate, i.e., they do not appear just before a tachyarrhythmia nor do they resolve with appropriate therapy. However, with sufficient processing capability within the implanted device, including the appropriate filters, continuous on-line monitoring is possible similar to that which has been done using surface leads and electrodes that this parameter holds promise for being potential marker for preemptive tachyarrhythmia pacing.

D. Electrical Alternans of the QT interval. Another marker that may be used as an indicator for increased vulnerability to ventricular tachyarrhythmias is the electrical alternans of the QT interval. The electrical alternans of the heart is generally defined as a disorder in which the ventricular complexes, e.g., the QT interval, are regular in time, but of an alternating pattern. The existence of the electrical alternans of the QT interval has to do with temporal dispersion of refractoriness which, while one cause is a bradycardia and another is ischemia, other causes may also exist. Thus, through monitoring the QT interval, again based upon the intracardiac electrogram rather than the surface ECG, modification of therapy in a preemptive manner (e.g., increasing the heart rate to shorten the QT interval) may be possible, as may a much more aggressive therapy once a tachyarrhythmia has been identified. Again, while some literature mentions the QT interval alternans as a diagnostic marker based upon the surface ECG, no one to Applicants' knowledge has proposed making this assessment from the intracardiac EGM, nor using this information to modify therapy.

From the above, it is thus seen that, e.g., the late potentials as detected by SAEGM and/or the HRV may be used to modify the system's response to a tachyarrhythmia, particularly in a tachyarrhythmia-based product. For example, a dramatic reduction in HRV may be used to allow the device to intervene earlier or more vigorously in response to an identified tachycardia. By the same token, a patient with late potentials indicating an area of slow conduction within the myocardium predisposing to a stable reentrant tachycardia (monomorphic ventricular tachycardia) may respond to standard antitachycardia pacing (ATP). Contrariwise, a patient without late potentials or one who demonstrates the markers for active ischemia is likely to develop a more unstable and chaotic rhythm, thus warranting a more vigorous initial intervention as with a high energy shock rather than initially applying antitachycardia pacing or lower energy shocks (cardioversion).

Advantageously, use of the microprocessor-based implantable stimulation device, such as ICD 20 and pacemaker 70, as shown in FIGS. 1 and 2 permits a great deal of flexibility in how the present invention is implemented and carried out. For example, the particular parameters monitored and used to trigger the selected preemptive tachyarrhythmia pacing (PTP) algorithm may be programmably selected. Similarly, how much of an abrupt change from the norm is required before the preemptive tachyarrhythmia pacing algorithm is invoked, and how long such algorithm remains invoked, may be programmably set. Likewise, the particular preemptive tachyarrhythmia pacing algorithm triggered when an abrupt change occurs in the monitored parameter(s) may be modified as required to best suit the needs of a particular patient. Indeed, by using a programmable microprocessor as the main control element within the stimulation device, there is virtually no limit to the types of parameters that may be monitored during the cardiac cycle and the types of preemptive tachyarrhythmia pacing algorithms that may be triggered whenever the monitored parameters suggest a notable change has occurred suggestive of an upcoming tachyarrhythmia.

While the invention herein disclosed has been described by means of specific embodiments and applications thereof, numerous modifications and variations could be made thereto by those skilled in the art without departing from the scope of the invention set forth in the claims.

APPENDIX A

This Appendix A sets forth additional background material which may help the reader better understand the underlying causes of a tachyarrhythmia and further better understand why the preemptive approach of the present invention is successful at preventing a tachyarrhythmia.

There are three common causes of pathologic tachyarrhythmias. These include: (1) enhanced automaticity; (2) triggered automaticity; and (3) reentry. A brief description of each of these causes follows.

The first mechanism by which a pathologic tachyarrhythmia is initiated is "enhanced automaticity". To better understand the concept of enhanced automaticity, it will first be helpful to explain automaticity. Automaticity is the ability of a group of cells in the heart to spontaneously depolarize. This has also been called spontaneous diastolic depolarization [SDD]. This signal is conducted to the surrounding tissue resulting in a propagated impulse. The rate of spontaneous discharge is affected by multiple factors including, but not limited to sympathetic and parasympathetic tone, arterial and venous oxygen saturation levels, stretch, temperature, and circulating catecholamines. Fluctuations in automaticity of the sinoatrial node (also called the sinus node while the resulting rhythm is sinus rhythm) is the prime controller of the normal heart rate. In addition to the sinoatrial node, tissues in the AV node, His Bundle, and ventricular specialized conduction system have cells which are capable of spontaneous depolarization. The SDD of these other tissues occur at progressively slower rates than the sinus node such that they are repeatedly reset by the usually more rapid sinus node discharge. If the sinus node fails due to either disease or extrinsic factors such as pharmacologic agents, then the lower foci with pacemaker capability (another name for automaticity) will take over. There is a hierarchy with the AV junctional tissues have a faster rate than those tissues located deep in the ventricle (ventricular specialized conduction system). These lower native pacemaker tissues would be analogous to a VVI pacemaker being repeatedly reset by a faster intrinsic heart rhythm, but should the native heart rate fail, the pacemaker will provide back-up protection to prevent asystole.

The rate of discharge of those cells which already have the ability to spontaneously initiate a cardiac depolarization as well as altered abnormal tissues, which may acquire this capability may accelerate their rate due to a pathologic process. This effectively causes these tissues to usurp control from the intrinsic sinus mechanism. This is termed "enhanced automaticity". This is estimated to account for approximately ten percent of all pathologic tachyarrhythmias.

The second mechanism by which a pathologic tachyarrhythmia is initiated is "triggered automaticity". In this setting, a group of pathologic cells is capable of spontaneous diastolic depolarization, but only after a critically timed premature beat occurs. Hence the tachyarrhythmia must be triggered. This is believed to be the mechanism for the pathologic tachyarrhythmias associated with digitalis intoxication as well as those associated with the Long QT Syndrome. As a group, rhythms due to triggered automaticity are believed to account for less than one percent of all tachyarrhythmias.

The third mechanism which is estimated to account for ninety percent of all organized pathologic tachyarrhythmias is "reentry". The concept of reentry is based upon two critical conduction pathways. These pathways have different recovery and conduction times. Clinically, these rhythms are initiated by a premature beat, which finds one of the critical pathways totally refractory and unable to conduct an impulse. The second pathway while capable of conducting, commonly conducts very slowly. This same pathway recovers very quickly (call this the alpha pathway). By the time the impulse exits the alpha pathway, it finds the second or beta pathway now fully recovered and capable of conducting an impulse. The impulse is propagated up (in a backward direction) through the beta pathway at a relatively rapid speed. By the time it exits this pathway, it now finds the alpha pathway recovered and able to again conduct in a forward direction at the original very slow speed. Given critical timing between the conduction and recovery times for these two pathways, a tachycardia can be initiated which is sustained by the impulse continually traveling in a circular pattern. Common examples of reentrant tachycardias include atrial flutter where the pathway involves the entire right atrium, AV nodal reentry where the pathway involves tissues in and around the AV node, AV reentry where one pathway comprises the AV node—His Bundle and the second pathway is a congenital muscular bridge between the atrium and ventricle termed a Kent Bundle or less frequently Mahaim or James fibers. This latter condition is commonly known as the Wolff-Parkinson-White syndrome. Monomorphic ventricular tachycardia is also an example of reentry. Reentrant tachycardias can occur in any tissue of the heart and after a period of rapid repeated depolarization, may degenerate into fibrillation, either atrial or ventricular.

The hallmark of a reentrant rhythm is two conducting pathways, one of which demonstrates unidirectional block (the block in conduction in one direction only allowing conduction in the opposite direction). It is identified in the Electrophysiology Laboratory by its ability to be both initiated by a critically timed premature beat as well as terminated by a critically timed premature beat. Treatment of these rhythms has been directed at pharmacologically altering the substrate which allows them to occur (changing conduction or recovery times of the critical tissues) or pharmacologically suppressing the trigger or initiating event that is commonly a premature beat, either atrial or ventricular depending upon the site of the tachycardia. Treatment has also included termination of the tachycardia once it has occurred. This may be accomplished with physiologic phenomena that may alter either conduction or recovery times in the critical pathway (for example, self-induced gagging or carotid sinus massage increases vagal tone and slows conduction and recovery in sinus and AV nodal tissues), acute administration of pharmacologic agents (for example, intravenous adenosine or verapamil), antitachycardia pacing and external or internal cardioversion. The critical pathways have also been identified and intentionally destroyed as with radio-frequency ablation delivered via a temporary pacing catheter or surgically via a scalpel.

The events which most often initiate the reentrant and triggered tachycardias are premature beats, either atrial or ventricular. The occurrence of premature beats is enhanced by a number of factors including factors which increase .automaticity of tissues with intrinsic pacemaker capability. Slow heart rates (bradycardias) also increase the likelihood of a premature depolarization. The mechanism by which slow heart rates, even heart rates which are only relatively slow for the given physiologic state, is believed to contribute to premature beats is a phenomenon termed temporal dispersion of refractoriness. The cardiac action potential duration [APD] (grossly estimated by the QT interval for the ventricle) is dependent upon the heart rate. The QT interval is directly related to the interval associated with the intrinsic cardiac rhythm—fast rates have a short interval between consecutive complexes resulting in a shortening of the QT interval where as slow rates have a long interval between complexes and the QT interval is increased. There is a formula which normalizes the QT interval for rate and this is termed the Bazett's formula. The majority of the APD is the recovery or repolarization time which comprises phases 2 and 3 of the APD. The longer the repolarization times also means that multiple different tissues in that cardiac chamber (atrium or ventricle) may be out-of-phase with one another predisposing to local reentry for one cycle or the occurrence of boundary currents which allow a partially recovered cell to initiate depolarization from a contiguous fully recovered cell, thus propagating a second impulse that if critically timed can then trigger a reentrant tachycardia with the appropriate substrate of tissue (two larger pathways).

The fact that slow heart rates may predispose to premature beats, which can then initiate a tachycardia has been well documented with respect to both ventricular and supraventricular rhythms. There is the "Rule of Bigeminy" where a single premature beat is followed by a pause (relative bradycardia) which then allows for another premature beat following the complex which terminates the pause. This "rule" was detailed in an article by Pick, Langendorf and Winternitz in the journal Circulation in 1955 with respect to ventricular ectopy. There is also Killip's Rule which states that an atrial premature beat occurring closer than 50% of the preceding sinus cycle has a greater chance of initiating a supraventricular tachycardia than one which occurs with a coupling interval, which is greater than 60% of the preceding sinus cycle length. The tachycardias that occur in the setting of an absolute or relative bradycardia include the paroxysmal supraventricular tachyarrhythmias that are an integral part of the Bradycardia-Tachycardia Syndrome [BTS], a subset of the Sick Sinus Syndrome [SSS]; and Torsade de Pointes or polymorphic ventricular tachycardia associated with a long QT interval, either acquired or as a part of the Congenital Long QT Syndrome.

It is known in the art that atrial or dual-chamber pacing in patients with sinus node dysfunction produces a reduced incidence of atrial fibrillation and other supraventricular tachycardias. The presumed mechanism is "overdrive suppression" where the paced rate, which is faster than the intrinsic rhythm reduces the temporal dispersion of refractoriness in the critical tissues (in this case, the atrium). This reduces the incidence of premature beats eliminating or minimizing the trigger for the supraventricular tachycardias. It may also allow for a more homogenous pattern of recovery thus minimizing the chance of two distinct conducting pathways.

A bradycardia may be relative with respect to the given physiologic state, for example, a heart rate of 90 beats per minute [bpm] would be a relative bradycardia when the patient required a heart rate of 110 bpm. Increases in heart rate are commonly due to increased sympathetic activity which will also increase automaticity of ectopic foci that have the capability of spontaneous diastolic depolarization. Premature beats can also occur at these more rapid rates to trigger a tachycardia. It has been recently reported that dual-chamber rate modulated pacing, specifically DDIR, was associated with a lower incidence of atrial arrhythmias than standard dual-chamber pacing (DDI) in a group of patients with sinus node dysfunction and chronotropic incompetence such that they did not increase their heart rate on their own.

Further, while a single premature beat may initiate a tachycardia, commonly (apropos of Torsade de Pointes associated with the Long QT Syndrome) the first premature beat rarely triggers a tachyarrhythmia. Rather, the first premature beat is followed by a relatively longer cycle which increases temporal dispersion of refractoriness triggering a second premature beat. This process continues until repetitive forms begin to occur and finally a sustained tachycardia develops.

What is claimed is:

1. A method of operating an implantable medical device in one of a main operating mode or a preemptive tachyarrhythmia preventive pacing operating mode, the implantable medical device including pulse generating means for generating pacing pulses and directing such pulses to cardiac tissue of a patient, the pulse generating means being controlled by a processor, the processor being coupled to a memory wherein an operating program for controlling the operating modes may be stored, the method comprising the steps of:

(a) sensing at least one parameter associated with the physiology of the patient's heart for an indication that a tachyarrhythmia may soon occur;

(b) determining when the at least one parameter exceeds a prescribed threshold, thereby indicating that a tachyarrhythmia may soon occur;

(c) automatically operating the implantable medical device in accordance with the main operating mode whenever the at least one parameter suggests that a tachyarrhythmia may not soon occur, wherein the main operating program is aimed at controlling the implantable medical device so that it performs its intended function; and (d) automatically operating the implantable medical device in accordance with the preemptive tachyarrhythmia preventive pacing operating mode whenever the at least one parameter exceeds the prescribed threshold thereby indicating that a tachyarrhythmia may soon occur, wherein the preemptive tachyarrhythmia preventive pacing operating mode is aimed at preventing a tachyarrhythmia from occurring.

2. The method, as set forth in claim 1, wherein the step of sensing the at least one parameter for an indication that a tachyarrhythmia may soon occur comprises:

sensing a first value of a first parameter at a time when a tachyarrhythmia is not present, the first value being indicative of a normal, non-tachyarrhythmia, condition; and storing the first value of the first parameter indicative of a normal, non-tachyarrhythmia, condition as a reference value; and sensing a second value of the first parameter during subsequent cardiac cycles of the patient; and wherein the determining step comprises:

comparing the second value of the first parameter to the reference value;

defining the patient's rhythm as one in which a tachyarrhythmia may soon occur when the first parameter has changed by at least a prescribed amount from the reference value; and defining the patient's rhythm as one in which a tachyarrhythmia may not soon occur when the first parameter has not changed by at least a prescribed amount from the reference value.

3. The method, as set forth in claim 1, wherein the step of sensing the at least one parameter for an indication that a tachyarrhythmia may soon occur comprises:

sensing a first set of values for a first set of parameters at a time when a tachyarrhythmia is not present, the first set values being indicative of a normal, non-tachyarrhythmia, condition;

storing the first set of values of the first set of parameters at the time when a tachyarrhythmia is not present as a reference template; and sensing a second set of values for the first set of parameters during subsequent cardiac cycles of the patient; and wherein the determining step comprises:

comparing the first set of values of the first set of parameters during a subsequent cardiac cycle to the reference template;

defining the patient's rhythm as one in which a tachyarrhythmia may soon occur when the first set of parameters has changed by at least a prescribed amount from the reference template; and defining the patient's rhythm as one in which a tachyarrhythmia may not soon occur when the first set of parameters has not changed by at least a prescribed amount from the reference template.

4. The method, as set forth in claim 1, wherein the preemptive tachyarrhythmia pacing operating mode comprises operating in an overdrive pacing mode.

5. The method, as set forth in claim 4, wherein operating in an overdrive pacing mode comprises setting a pacing rate based on a predetermined diurnal rate.

6. The method, as set forth in claim 4, further comprising automatically determining a diurnal rate, and operating in an overdrive pacing mode by setting a pacing rate based on the automatically determined diurnal rate.

7. The method, as set forth in claim 6, wherein automatically determining the diurnal rate comprises gathering heart rate data over at least a 24-hour period, filtering the heart rate data with a digital recursive low-pass filter using a delay of at least 20 seconds, and using the resulting filtered output as an indicator of the diurnal rate.

8. The method, as set forth in claim 7, wherein the diurnal rate comprises a diurnal base rate (DBR), and wherein determining the diurnal base rate comprises:

setting a desired "Sleeprate" parameter as a desired heart rate to be allowed when sleeping;

computing a running average of the gathered heart rate data at prescribed increments of "Delay2" seconds;

finding a difference, "DIFF2(t)", between the running average after each prescribed increment of "Delay2" seconds;

determining an effective time constant, "ACT_SD2(t)", after each prescribed increment of "Delay2" seconds, as ACT_SD2(t)=(1/j) [DIFF2(t)]+[(j-1)/j]ACT_SD2(t-Delay2), where j is an integer having a value of at least 30, and ACT_SD2(t-Delay2) is the most recent value of the effective time constant determined during the most-recent increment prior to the present increment;

computing the diurnal base rate (DBR) corresponding to the prescribed increment as DBR(t)=Slope2[ACT_SD2(t)]+Sleeprate, where "Slope2" is a predetermined parameter.

9. The method, as set forth in claim 8, further comprising selecting the value of "Delay2" to be at least 25 seconds, and setting the value of "j" to be at least 60.

10. The method, as set forth in claim 8, further comprising selecting the value of "Delay2" to be a prescribed number, n2, of cardiac cycles, where n2 is at least 30.

11. The method, as set forth in claim 4, wherein the preemptive tachyarrhythmia pacing operating mode comprises operating in an atrial overdrive pacing mode.

12. The method, as set forth in claim 11, wherein operating in the atrial overdrive pacing mode comprises setting a pacing rate based on an automatic stepped increase over an average atrial rate.

13. The method, as set forth in claim 12, further comprising:

(a) determining the average atrial rate by monitoring at least three consecutive P-to-P intervals;

(b) setting the pacing rate to a new base rate value that is a prescribed step increase greater than the average atrial rate;

(c) pacing the atria at a rate faster than the new base rate value for a prescribed number $n_P$ of cardiac cycles; and (d) returning to the new base rate value after the prescribed number $n_P$ of cardiac cycles.

14. The method, as set forth in claim 13, wherein the number of cardiac cycles $n_P$ that are paced faster than the new base rate value comprises at least three.

15. The method, as set forth in claim 13, wherein step (c) comprises pacing the atria at a rate that is both faster than the new base rate value and that varies from cycle to cycle for each of the $n_P$ cardiac cycles.

16. The method, as set forth in claim 15, further comprising pacing the atria at a rate that is increasingly faster than the new base rate value for each of the $n_P$ cardiac cycles.

17. The method, as set forth in claim 15, further comprising pacing the atria at a rate that is decreasingly faster than the new base rate value for each of the $n_P$ cardiac cycles.

18. The method, as set forth in claim 15, further comprising pacing the atria at a rate that is randomly faster than the new base rate value for each of the $n_P$ cardiac cycles.

19. The method, as set forth in claim 13, wherein the prescribed step increase above the average atrial rate to which the new base rate value is set comprises at least 5 bpm.

20. The method, set forth in claim 13, further comprising periodically decreasing the atrial pacing rate to test for the occurrence of P-waves; and if P-waves are detected, determining the average atrial rate by monitoring at least three consecutive P-to-P intervals and resetting the pacing rate to yet a newer base rate value that is a prescribed step increase greater than the most-recently determined average atrial rate, whereby the base rate value is dynamically reset as needed as a function of the most-recently determined average atrial rate.

21. The method, as set forth in claim 11, wherein operating in the atrial overdrive pacing mode comprises setting a pacing rate using a negative hysteresis scheme.

22. The method, as set forth in claim 21, further comprising:

setting the atrial pacing rate at a programmed base rate or a sensor indicated rate, whichever is faster;

increasing the atrial pacing rate to an atrial hysteresis rate, where the hysteresis rate is a programmed amount delta greater than the faster of the programmed base rate or the sensor-indicated rate, whenever an intrinsic P-wave is sensed within an atrial escape interval of the current cardiac cycle so that the next cardiac cycle is subjected to the atrial hysteresis rate;

maintaining the atrial hysteresis rate for at least one cardiac cycle; and returning the atrial pacing rate to the faster of the programmed base rate or the sensor-indicated rate.

23. The method, as set forth in claim 22, further comprising returning the atrial pacing rate to the faster of the programmed base rate or the sensor-indicated rate in one step so that the following cardiac cycle is subjected to the faster of the programmed base rate or the sensor-indicted rate.

24. The method, as set forth in claim 22, further comprising returning the atrial pacing rate to the faster of the programmed base rate or the sensor-indicated rate gradually over several cardiac cycles.

25. The method, as set forth in claim 1, wherein the preemptive tachyarrhythmia preventive pacing operating mode aimed at preventing a tachyarrhythmia from occurring comprises introducing randomicity into a base rate of the implantable medical device.

26. The method, as set forth in claim 25, further comprising:

gathering heart rate data;

processing the gathered heart rate data to determine a correlation dimension, $D_2$; and varying the pacing rate of the pacing pulses applied to the cardiac tissue to maintain $D_2$ above a prescribed correlation dimension threshold level.

27. The method, as set forth in claim 26, further comprising adjusting the pacing rate as required to maintain correlation dimension $D_2$ above a value of about 2.0.

28. The method, as set forth in claim 26, further comprising adjusting the pacing rate as required to maintain overdrive pacing and to maintain $D_2$ above a value of about 2.0.

29. The method, as set forth in claim 1, further comprising switching the operating mode of the implantable medical device from its main operating mode to a preemptive operating mode whenever a tachyarrhythmia is determined to soon occur.

30. The method, as set forth in claim 29, wherein the at least one parameter that suggests a tachyarrhythmia may soon occur is selected from a group of physiological parameters that includes: blood pressure, contractility, pre-ejection interval, intra-chamber impedance, stroke volume, and oxygen saturation.

31. The method, as set forth in claim 29, wherein sensing the at least one parameter which suggests a tachyarrhythmia may soon occur comprises sensing the patient's heart rate variability; and wherein the determining step comprises determining a marked reduction in heart rate variability (HRV).

32. The method, as set forth in claim 29, wherein sensing the at least one parameter which suggests a tachyarrhythmia may soon occur comprises sensing the patient's right ventricular electrogram through a single endocardial lead; and wherein the determining step comprises determining high frequency cardiac activity signals above the prescribed threshold thereby indicating the presence of ischemia.

33. The method, as set forth in claim 29, wherein sensing the at least one parameter which suggests a tachyarrhythmia may soon occur comprises sensing the patient's right ventricular electrogram through a single endocardial lead; and wherein the determining step comprises determining electrical alternans of the QT interval above the prescribed threshold.

34. A method of operating an implantable tissue-stimulating medical device in a preemptive tachyarrhythmia pacing mode for the purpose of preventing the occurrence of a tachyarrhythmia, said method comprising:

sensing a value of at least one physiological condition capable of predicting the occurrence of a tachyarrhythmia;

detecting when the value of the at least one physiological condition provides an indication that a pre-tachycardia condition exists; and when such pre-tachyarrhythmia condition is detected, modifying the behavior of the implantable tissue-stimulating medical device so as to minimize the likelihood of occurrence of a tachyarrhythmia.

35. The method, as set forth in claim 34, further including returning the behavior of the implantable tissue-stimulating medical device to what it was before being modified in response to detecting the pre-tachyarrhythmia condition upon the occurrence of a prescribed event.

36. The method, as set forth in claim 35, further comprising returning the behavior of the implantable tissue-stimulating medical device to what it was initially upon a timing out of a prescribed period of time, whereby the behavior of the implantable tissue-stimulating medical device is modified for only the prescribed period of time.

37. The method, as set forth in claim 35, further comprising returning the behavior of the implantable tissue-stimulating medical device to what it was initially upon the completion of a prescribed number of consecutive cardiac cycles.

38. The method, as set forth in claim 35, further comprising returning the behavior of the implantable tissue-stimulating medical device to what it was initially upon detecting the absence of the pre-tachyarrhythmia condition.

39. The method, as set forth in claim 35, further comprising returning the behavior of the implantable tissue-stimulating medical device to what it was initially upon detecting the return of a sensed parameter back to a value it had before the pre-tachyarrhythmia condition was detected.

40. The method, as set forth in claim 34, wherein the step of modifying the behavior of the implantable tissue-stimulating medical device comprises introducing a degree of randomicity into the stimulation rate of the device so that a minimum specified correlation dimension is maintained.

41. The method, as set forth in claim 34, wherein the step of modifying the behavior of the implantable tissue-stimulating medical device comprises switching its operating mode.

42. The method, as set forth in claim 34, wherein the implantable tissue-stimulating device comprises a device adapted to stimulate cardiac tissue, and wherein the step of modifying the behavior of the implantable tissue-stimulating medical device comprises operating the device in an overdrive pacing mode which provides stimulation pulses at a rate faster than a natural underlying heart rate.

43. The method, as set forth in claim 42, wherein overdrive pacing comprises pacing at a rate that is a prescribed amount faster than an automatically determined diurnal rate.

44. The method, as set forth in claim 42, wherein overdrive pacing comprises pacing at a rate that is an automatic stepped increase over an average heart rate.

45. The method, as set forth in claim 42, wherein overdrive pacing comprises pacing every cardiac cycle using a negative hysteresis scheme.

46. The method, as set forth in claim 34, wherein the implantable tissue-stimulating medical device comprises a device adapted to stimulate cardiac tissue of a patient in order to maintain a desired heart rhythm, and wherein the step of detecting a pre-tachyarrhythmia condition comprises:

monitoring, during a time when the patient is at rest and the cardiac rhythm is stable, cardiac events of the patient for a sufficiently long period of time to learn a particular sequence and rate of cardiac events that can thereafter be used to represent a normal condition for the patient; and detecting, after learning the sequence and rate of cardiac events that represent a normal condition for the patient, the pre-tachyarrhythmia condition as any cardiac events that vary a prescribed amount from the learned sequence and rate of cardiac events representing a normal condition for the patient.

47. The method, as set forth in claim 34, wherein the implantable tissue-stimulating medical device comprises a device adapted to stimulate cardiac tissue of a patient in order to maintain a desired heart rhythm, and wherein the step of detecting a pre-tachyarrhythmia condition comprises:

monitoring, during a time when the patient is not experiencing a tachyarrhythmia, at least one physiological parameter of the patient and saving the value of such at least one physiological parameter as a threshold reference; and detecting, after saving the threshold reference, the pre-tachyarrhythmia condition by continuing to monitor the at least one physiological parameter and detecting when its monitored value differs from the threshold reference by more than a prescribed amount.

48. The method, as set forth in claim 47, wherein the at least one physiological parameter is selected from a group of cardiac-related physiological parameters comprising: blood pressure, heart rate, blood temperature, blood $O_2$ saturation, contractility, pre-ejection interval, intra-chamber impedance, stroke volume, heart rate variability, and detection of ischemia.

49. A method of operating an implantable tissue-stimulating device, the device having generating means for generating electrical stimulating pulses of specified energies and applying the pulses to body tissue at specified times, and means for sensing natural muscle contractions of the body tissue, the method comprising:

predicting when a tachyarrhythmia may occur; operating in a preemptive tachyarrhythmia pacing mode whenever a tachyarrhythmia is predicted to occur, the preemptive tachyarrhythmia pacing mode triggering the generation of electrical stimulating pulses to the tissue at controlled times and energy levels designed to minimize the occurrence of a tachyarrhythmia in the tissue being stimulated; and operating the tissue-stimulating device in a non-preemptive tachyarrhythmia pacing mode whenever a tachyarrhythmia is not predicted to occur.

50. The method, as set forth in of claim 49, further comprising sensing at least one body parameter over a specified period of time;

determining whether the at least one body parameter satisfies specific criteria, the specific criteria defining a threshold condition which, when exceeded, is indicative of a body tissue condition conducive to the occurrence of a tachyarrhythmia;

operating the tissue-stimulating device in the preemptive tachyarrhythmia pacing mode when the at least one body parameter satisfies the specific criteria; and operating the tissue-stimulating device in the non-preemptive tachyarrhythmia pacing mode when the at least one body parameter does not satisfy the specific criteria.

51. An implantable cardiac tissue-stimulating device comprising:

pulse generating means for generating electrical stimulating pulses of specified energies;

lead/electrode means for delivering the stimulating pulses to cardiac tissue;

sensing means for sensing natural muscle contractions of the cardiac tissue;

means for determining when a pre-tachycardia condition exists; and processing/control means for operating in a preemptive tachyarrhythmia pacing mode when the pre-tachyarrhythmia condition exists and in a non-preemptive mode when the pre-tachyarrhythmia does not exist, the preemptive tachyarrhythmia pacing mode comprising means for triggering the pulse generating means of the tissue-stimulating device to apply electrical stimulating pulses to the cardiac tissue at controlled times and energy levels designed to minimize the occurrence of a tachyarrhythmia in the tissue being stimulated.

52. The implantable cardiac tissue-stimulating device, as set forth in claim 51, wherein:

the means for determining when a pre-tachycardia condition includes:

means for sensing at least one body parameter over a specified period of time; and means for determining whether the at least one body parameter satisfies specific criteria, the specific criteria defining a threshold condition which when exceeded is indicative of a body tissue condition conducive to the occurrence of a tachyarrhythmia; and the processing/control means includes:

means for operating the tissue-stimulating device in accordance with the preemptive tachyarrhythmia pacing mode when the at least one body parameter satisfies the specific criteria; and means for not operating the tissue-stimulating device in accordance with the non-preemptive tachyarrhythmia pacing mode when the at least one body parameter does not satisfy the specific criteria.

53. The implantable cardiac tissue-stimulating device, as set forth in claim 51, wherein the means for determining when a pre-tachycardia condition includes:

means for learning a normal sequence and rate of cardiac events at a time when the patient's cardiac rhythm is stable;

storing the normal sequence and rate of cardiac events; and means for detecting as the pre-tachyarrhythmia condition any cardiac events that vary a prescribed amount from the normal sequence and rate of cardiac events.

54. The implantable cardiac tissue-stimulating device, as set forth in claim 51, wherein the means for determining when a pre-tachycardia condition includes:

means for learning a normal heart rate variability during a time when the patient's cardiac rhythm is stable;

storing the normal heart rate variability; and means for detecting as the pre-tachyarrhythmia condition a heart rate variability that varies a prescribed amount from the normal heart rate variability.

55. The implantable cardiac tissue-stimulating device, as set forth in claim 51, wherein the means for determining when a pre-tachycardia condition includes:

means for learning a normal correlation dimension during a time when the patient's cardiac rhythm is stable;

storing the normal correlation dimension; and means for detecting as the pre-tachyarrhythmia condition a correlation dimension that varies a prescribed amount from the normal correlation dimension.

56. The implantable cardiac tissue-stimulating device, as set forth in claim 51, wherein the means for determining when a pre-tachycardia condition includes:

means for learning a normal a QT interval during a time when the patient's cardiac rhythm is stable;

storing the normal QT interval; and means for detecting as the pre-tachyarrhythmia condition alternans which occur in the QT interval that differ by a prescribed amount from the normal QT interval.

57. The implantable cardiac tissue-stimulating device, as set forth in claim 51, wherein the means for determining when a pre-tachycardia condition includes:

means for learning normal frequency components of a ventricular cardiac signal during a time when the patient's cardiac rhythm is stable;

storing the normal frequency components of the ventricular cardiac signal; and means for detecting as the pre-tachyarrhythmia condition high frequency cardiac signal components which differ by a prescribed amount from the normal frequency components of the ventricular cardiac signal, the high frequency cardiac signal components indicating the presence of ischemia.

58. The implantable cardiac tissue-stimulating device, as set forth in claim 51, wherein the processing/control means for operating in a preemptive tachyarrhythmia pacing mode comprises:

means for operating in an overdrive mode which provides stimulation pulses at a rate faster than a natural underlying heart rate.

59. The implantable cardiac tissue-stimulating device, as set forth in claim 58, wherein the means for operating in the overdrive mode comprises:

means for providing stimulation pulses at a varying rate faster than a natural underlying heart rate.

60. The implantable cardiac tissue-stimulating device, as set forth in claim 58, wherein the means for operating in the overdrive mode comprises:

means for providing stimulation pulses at a randomly-varying rate faster than a natural underlying heart rate.

61. The implantable cardiac tissue-stimulating device, as set forth in claim 58, wherein:

the means for determining when a pre-tachycardia condition exists includes means for determining a normal correlation dimension during a time when the patient's rhythm is stable; and the means for operating in the overdrive mode includes means for providing stimulation pulses at a rate which maintains correlation dimension to within a prescribed range about the normal correlation dimension.

62. The implantable cardiac tissue-stimulating device, as set forth in claim 58, wherein:

the means for determining when a pre-tachycardia condition exists includes means for determining a normal heart rate variability during a time when the patient's rhythm is stable; and the means for operating in the overdrive mode includes means for providing stimulation pulses at a rate which mimics the normal heart rate variability.

* * * * *